US008604206B2

(12) United States Patent
Boyd et al.

(10) Patent No.: US 8,604,206 B2
(45) Date of Patent: Dec. 10, 2013

(54) COMPOSITIONS FOR PREVENTING AND/OR TREATING DEGENERATIVE DISORDERS OF THE CENTRAL NERVOUS SYSTEM

(75) Inventors: Robert Boyd, Horsham, PA (US); Gary Lee, West Windsor, NJ (US); Philip Rybczynski, Branchburg, NJ (US)

(73) Assignee: Amicus Therapeutics, Inc., Cranbury, NJ (US)

( * ) Notice: Subject to any disclaimer, the term of this patent is extended or adjusted under 35 U.S.C. 154(b) by 369 days.

(21) Appl. No.: 12/898,112

(22) Filed: Oct. 5, 2010

(65) Prior Publication Data

US 2011/0092541 A1 Apr. 21, 2011

Related U.S. Application Data

(60) Provisional application No. 61/252,803, filed on Oct. 19, 2009.

(51) Int. Cl.
*C07D 211/46* (2006.01)
*A61K 31/445* (2006.01)

(52) U.S. Cl.
USPC ........... 546/219; 546/220; 546/242; 514/315; 514/328

(58) Field of Classification Search
USPC .................. 546/242, 219, 220; 514/315, 328
See application file for complete search history.

(56) References Cited

U.S. PATENT DOCUMENTS

| | | | |
|---|---|---|---|
| 5,863,903 | A | 1/1999 | Lundgren et al. |
| 6,274,597 | B1 | 8/2001 | Fan et al. |
| 6,774,135 | B2 | 8/2004 | Fan et al. |
| 2004/0082641 | A1 | 4/2004 | Rytved et al. |
| 2007/0270350 | A1 | 11/2007 | Singh |
| 2008/0009516 | A1 | 1/2008 | Wustman |

FOREIGN PATENT DOCUMENTS

| | | |
|---|---|---|
| EP | 1860101 A1 | 11/2007 |
| WO | 2004037233 | 5/2004 |
| WO | 2007150064 | 12/2007 |
| WO | 2010118282 | 10/2010 |

OTHER PUBLICATIONS

Tina M. Jespersen "Isofagomine, a Potent, New Glycosidase Inhibitor" Angewandte Chemie International Edition in English vol. 33, Issue 17, 1778-1779.*
Patani et. al. "Bioisosterism: A Rational Approach in Drug Design" Chemical Reviews 1996, 96, 3147-3176.*
Wakefield, Basil "Fluorinated Pharmaceuticals" Innovations in Pharmaceutical Technology 2003, 74, 76-78, Online "http://web.archive.org/web/20030905122408/http://www.iptonline.com/articles/public/IPTFOUR74NP.pdf." (accessed via Wayback machine Nov. 20, 2009 showing web availability as of Sep. 2003.).*
Chemical Abstracts Services Registry No. 1025932-08-4, 3,4-Piperidinediol, 5-(1-methylethyl)- indexed from the Database: ChemSpider on Jun. 6, 2008.*
Sun "A new asymmetric route to substituted piperidines: synthesis of N-alkyl-3,4-dihydroxy-5-alkylpiperidines" Tetrahedron Letters 41 (2000) 2801-2804.*
Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, pp. 451 and 596.*
Faugeroux "C-Alkyl 5-membered ring imino sugars as new potent cytotoxic glucosylceramide synthase inhibitors." Organic & Biomolecular Chemistry, 2006, 4(24), 4437-4439.*
International Search Report and Written Opinion for PCT/US10/51447, dated Nov. 6, 2010.
Jmoudiak et al., "Gaucher Disease: Pathological Mechanisms and Modern Management", British Journal of Hematology, 2005, 129:178-188.
Centre for Genetics Education [Online], "Autosomal Recessive Inheritance-Traditional Patterns of Inheritance", [Retrieved Nov. 6, 2012], Retrieved from the Internet: <URL: http://www.genetics.edu.au>, 2007, 1-3.
Vippagunta et al., "Crystalline Solids", Adv Drug Deliv Rev. May 16, 2001, 48(1):3-26.
International Search Report and Written Opinion issued in co-pending International Application No. PCT/US10/051458, mailed Nov. 18, 2010, Applicant: Amicus Therapeutics, Inc.
Office Action issued on Nov. 8, 2012 by Examiner Draper in co-pending U.S. Appl. No. 12/898,196.
Patterson et al: "Miglustat for treatment of Niemann-Pick C disease: a randomised controlled study", Lancet Neurology, Lancet Publishing Group, London, GB, vol. 6, No. 9, Aug. 14, 2007 , pp. 765-772, XP022200287, ISSN: 1474-4422, DOI: 10.1016/S1474-4422(07)70194.
Hidekazu Ouchi et al: "A New Route to Diverse 1-Azasugars from N -Boc-5-hydroxy-3-piperidene as a Common Building Block", The Journal of Organic Chemistry, vol. 70, No. 13, Jun. 2005, pp. 5207-5214, XP55059837, ISSN: 0022-3263, DOI: 10.1021/jo050519j.
Sun H et al: "A new asymmetric route to substituted piperidines: synthesis of N-alkyl-3,4-dihydroxy-5-alkylpiperidines", Tetrahedron Letters, Elsevier, Amsterdam, NL, vol. 41, No. 16, Apr. 1, 2000 , pp. 2801-2804, XP004195675, ISSN: 0040-4039, DOI: 10.1016/S0040-4039(00)00267-7.
Rives, Arnaud et al: "Enantioselective access to all-trans 5-alkylpiperidine-3,4-diols: application to the asymmetric synthesis of the 1-N-iminosugar (+)-isofagomine", Synthesis , (19), 3251-3258 CODEN: SYNTBF; ISSN: 0039-7881, 2009, XP002696027.
Imanishi, Takeshi et al: "1,6-Dihydro-3(2H)-pyridinones. IX. A regioselective synthesis of ethyl 3-methoxycarbonylmethyl-4-oxopiperidine-1-carboxylate from ethyl 3-hydroxy-1,2,3,6-tetrahydropyridine-1-carboxylate", Chemical & Pharmaceutical Bulletin , 31(11), 4135-8 CODEN: CPBTAL; ISSN: 0009-2363, 1983, XP002696028.
European Search Report dated Apr. 26, 2013, issued in co-pending European Application No./Patent No. 10825397.2-1453/2490533.
European Search Report dated May 13, 2013, issued in co-pending European Application No./Patent No. 10825396.4-1452/2490532.
Notice of Allowance dated May 7, 2013, issued by Examiner Draper in copending U.S. Appl. No. 12/898,196.

* cited by examiner

*Primary Examiner* — David K O Dell
(74) *Attorney, Agent, or Firm* — SorinRand LLP

(57) ABSTRACT

The present invention provides novel compounds as well as compositions and methods using the same for preventing and/or treating degenerative disorders of the central nervous system. In particular, the present invention provides methods for preventing and/or treating Parkinson's disease.

10 Claims, No Drawings

COMPOSITIONS FOR PREVENTING AND/OR TREATING DEGENERATIVE DISORDERS OF THE CENTRAL NERVOUS SYSTEM

CROSS-REFERENCE TO RELATED APPLICATION

This application claims the benefit of U.S. Provisional Application No. 61/252,803, filed Oct. 19, 2009, the contents of which is incorporated by reference herein.

FIELD OF THE INVENTION

The present invention provides novel compounds, known as pharmacological chaperones, as well as compositions and methods using the same for preventing and/or treating degenerative disorders of the central nervous system. In particular, the present invention provides methods for preventing and/or treating Parkinson's disease.

BACKGROUND OF THE INVENTION

Many degenerative disorders of the central nervous system are associated with pathologic aggregation of proteins or lipids. For example, synucleinopathies are a group of diseases that arise from disruption of synuclein protein homeostasis. In particular, alpha-synuclein aggregation is associated with pathological conditions characterized by Lewy bodies, such as Parkinson's disease, dementia with Lewy bodies, and multiple system atrophy. Likewise, alpha-synuclein fragment, non-Abeta component, is found in amyloid plaques of Alzheimer's disease. Recently, enhancement of glucocerebrosidase (beta-glucosidase; GCase) activity in the brain has been shown to prevent accumulation of synuclein in the brain (Sean Clark, Ying Sun, You-Hai Xu, Gregory Grabowski, and Brandon Wustman, "A biochemical link between Gaucher and Parkinson's disease and a potential new approach to treating synucleinopathies: a pharmacological chaperone for beta-glucocerebrosidase prevents accumulation of alpha-synuclein in a Parkinson's mouse model," Presented at the Society for Neuroscience Annual Meeting, San Diego, Calif., 2007). Thus, agents that enhance GCase activity may provide relief for patients at risk for developing or diagnosed with degenerative disorders of the central nervous system.

There is a need for new therapeutic compounds that can be used to prevent and/or treat degenerative disorders of the central nervous system that provide patients with a higher quality of life and achieve a better clinical outcome. In particular, there is a need for new therapeutic compounds to prevent and/or treat synucleinopathies such as Parkinson's disease and Alzheimer's disease that provide patients with a higher quality of life and achieve a better clinical outcome.

SUMMARY OF THE INVENTION

The present invention provides novel compounds as well as compositions and methods using the same to prevent and/or treat a degenerative disorder of the central nervous system in a patient at risk for developing or diagnosed with the same which includes administering to the patient in need thereof an effective amount of a compound described herein.

In one aspect, there is provided a compound as well as compositions and methods using the same to prevent and/or treat a degenerative disorder of the central nervous system in a patient at risk for developing or diagnosed with the same which includes administering to the patient in need thereof an effective amount of a compound defined by Formula I:

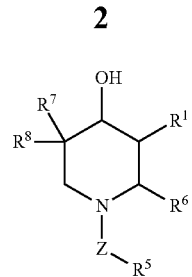

wherein:
$R^1$ is $C(R^2)(R^3)(R^4)$;
$R^2$ is hydrogen, —OH or halogen;
$R^3$ is hydrogen, —OH, halogen or $C_{1-8}$ alkyl;
$R^4$ is halogen, $C_{1-8}$ alkyl, substituted $C_{1-8}$ alkyl, aryl, substituted aryl, alkylcycloalkyl or substituted alkylcycloalkyl;
$R^3$ and $R^4$ may join with the carbon to which they are attached to form a cycloalkyl ring, which may be optionally substituted, preferably with halogen and more preferably with one or more fluorine atoms;
$R^6$ is hydrogen, $C_{1-8}$ alkyl, substituted $C_{1-8}$ alkyl, arylalkyl, substituted arylalkyl, alkylaryl, or substituted alkylaryl;
Z is optional, when present Z is —$(CH_2)_{1-8}$—, —C(=O)—, —S(=O)$_2$NH—, —S(=O)$_2$—, —C(=S)NH—, —S(=O)$_2$—CH$_3$, C(=O)—NH—, —S(=O)$_2$—NR$^9$R$^{10}$, —C(=O)C$_{1-8}$ alkyl or —C(=O)CH(NH$_2$)CH$_3$;
$R^9$ is hydrogen, $C_{1-8}$ alkyl or substituted $C_{1-8}$ alkyl;
$R^{10}$ is hydrogen, $C_{1-8}$ alkyl or substituted $C_{1-8}$ alkyl;
$R^5$ is hydrogen, $C_{1-8}$ alkyl, substituted $C_{1-8}$ alkyl, aryl, substituted aryl, $C_{1-8}$ alkenyl, substituted $C_{1-8}$ alkenyl, arylalkyl, substituted arylalkyl, alkylaryl, substituted alkylaryl, aminoarylalkyl or substituted aminoarylalkyl;
$R^7$ is —OH or halogen; and
$R^8$ is hydrogen, halogen or $C_{1-8}$ alkyl,
provided that $R^2$ and $R^3$ cannot both be hydrogen when $R^4$ is a halogen, Z is not present, $R^7$ is —OH, $R^5$, $R^6$ and $R^8$ are hydrogen.

In another aspect, there is provided a compound as well as compositions and methods using the same to prevent and/or treat a degenerative disorder of the central nervous system in a patient at risk for developing or diagnosed with the same which includes administering to the patient in need thereof an effective amount of a compound defined by Formula II:

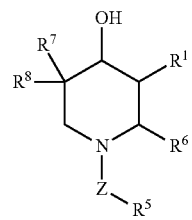

wherein:
$R^1$ is $C(R^2)(R^3)(R^4)$;
$R^2$ is hydrogen, —OH or halogen;
$R^3$ is hydrogen, —OH, halogen or —CH$_3$;
$R^4$ is halogen, —CH$_3$, phenyl, fluorophenyl, methylphenyl, cyclohexylmethyl, wherein when $R^4$ is a halogen, both $R^2$ and $R^3$ cannot be hydrogen;
$R^3$ and $R^4$ may join with the carbon to which they are attached to form a cycloalkyl ring, which may be optionally substituted with one or more halogen atoms;

$R^6$ is hydrogen, phenylalkyl or substituted phenylalkyl;

Z is optional, when present Z is —(CH$_2$)—, —C(=O)—, —S(=O)$_2$NH—, —S(=O)$_2$—, —S(=O)$_2$—CH$_3$, C(=O)—NH—, —S(=O)$_2$NR$^9$R$^{10}$, —C(=S)—NH— or —C(=O)$_2$—CH$_3$, $R^9$ is hydrogen or CH$_3$;

$R^{10}$ is hydrogen or CH$_3$;

$R^5$ is hydrogen or aminophenylalkyl;

$R^7$ is —OH or halogen; and $R^8$ is hydrogen, halogen or —CH$_3$, provided that $R^2$ and $R^3$ cannot both be hydrogen when $R^4$ is halogen, Z is not present, $R^7$ is —OH, $R^5$, $R^6$ and $R^8$ are hydrogen.

In yet another aspect, there is provided a compound as well as compositions and methods using the same to prevent and/or treat a degenerative disorder of the central nervous system in a patient at risk for developing or diagnosed with the same which includes administering to the patient in need thereof an effective amount of a compound defined by Formula III:

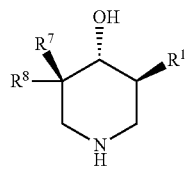

wherein:

$R^1$ is C(R$^2$)(R$^3$)(R$^4$);

$R^2$ is hydrogen, —OH or halogen;

$R^3$ is hydrogen, —OH, halogen or —CH$_3$;

$R^4$ is halogen, —CH$_3$, phenyl, fluorophenyl, methylphenyl, cyclohexylmethyl, wherein when $R^4$ is a halogen, both $R^2$ and $R^3$ cannot be hydrogen;

$R^3$ and $R^4$ may join with the carbon to which they are attached to form a cycloalkyl ring, which may be optionally substituted with one or more halogen atoms;

$R^7$ is —OH or halogen; and $R^8$ is hydrogen, halogen or —CH$_3$, provided that $R^2$ and $R^3$ cannot both be hydrogen when $R^4$ is a halogen, $R^7$ is —OH and $R^6$ and $R^8$ are hydrogen.

It is understood by a person of ordinary skill in the art that $R^2$, $R^3$ and $R^4$ in aforementioned Formulas I, II, and III will not be selected such that an unstable molecule will result.

In still another aspect, there is provided a compound as well as compositions and methods using the same to prevent and/or treat a degenerative disorder of the central nervous system in a patient at risk for developing or diagnosed with the same which includes administering to the patient in need thereof an effective amount of a compound selected from the following:

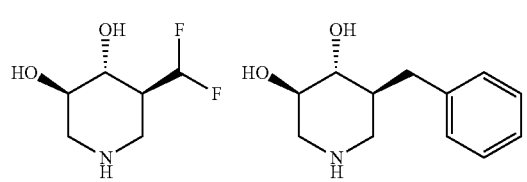

-continued

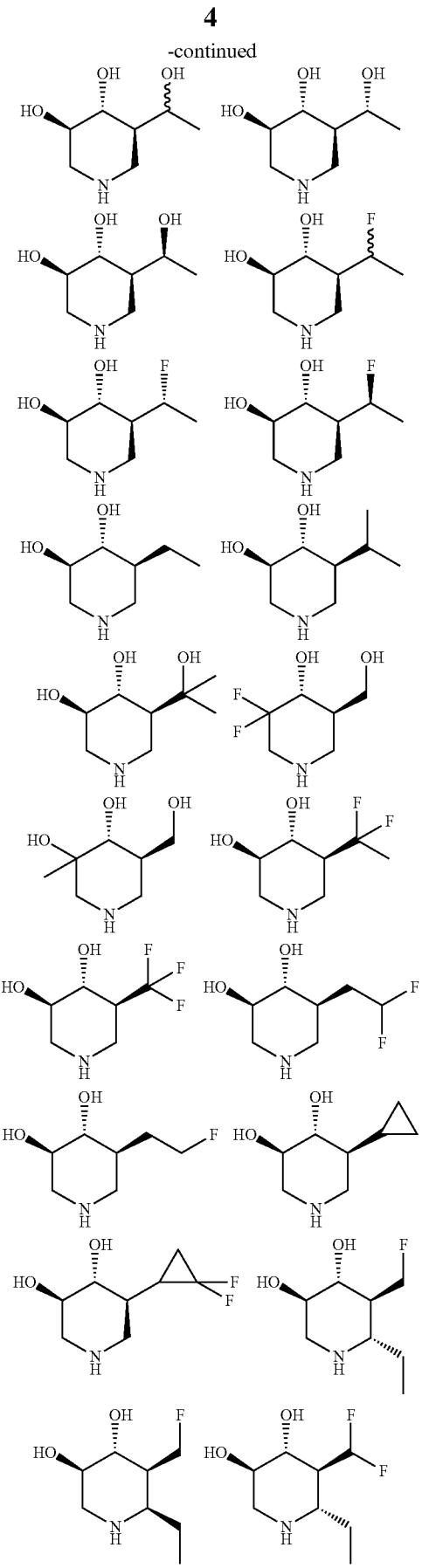

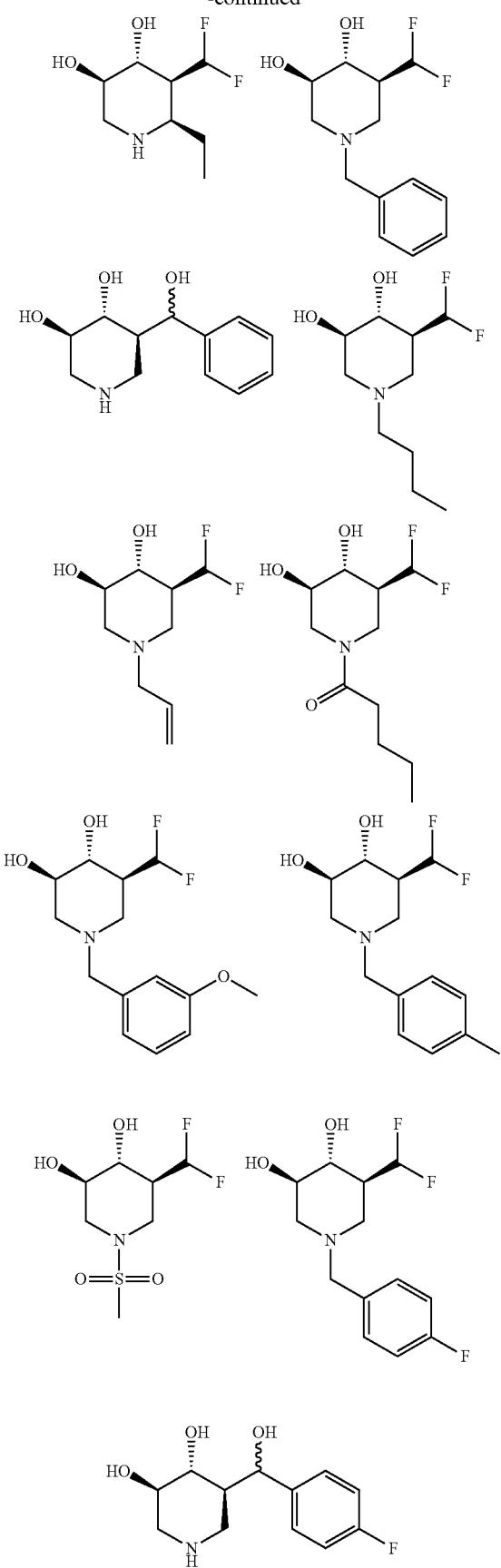
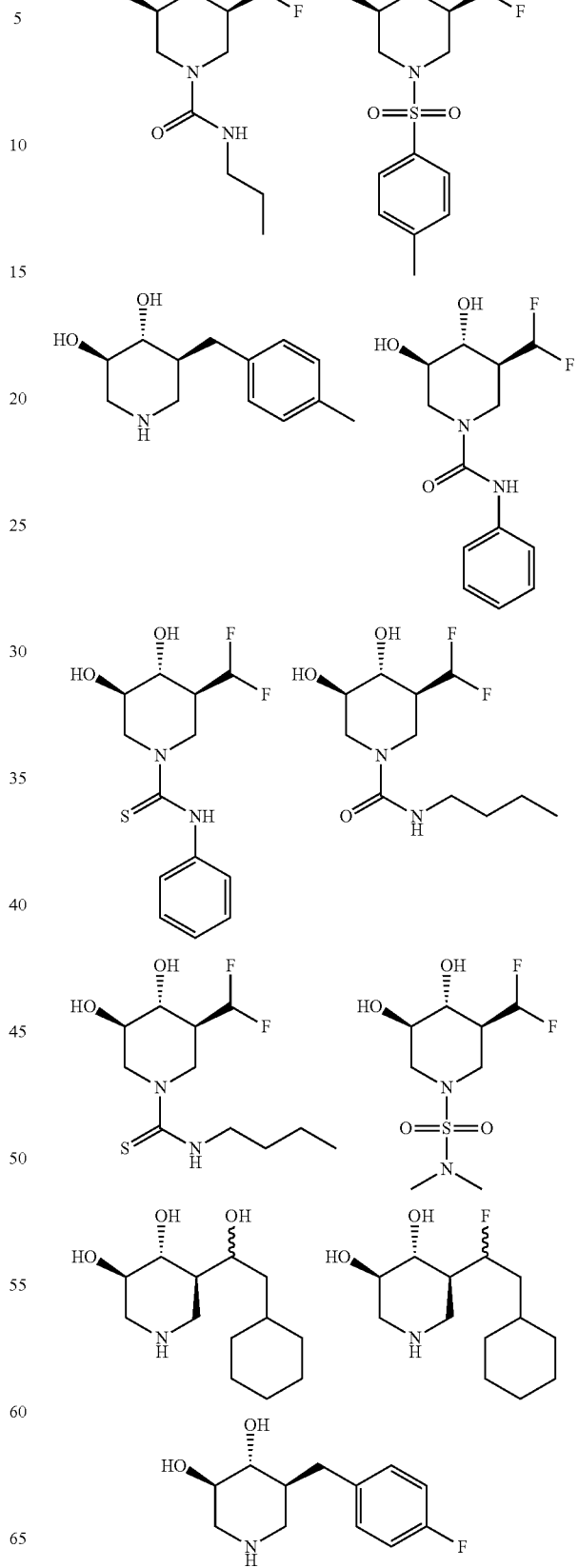

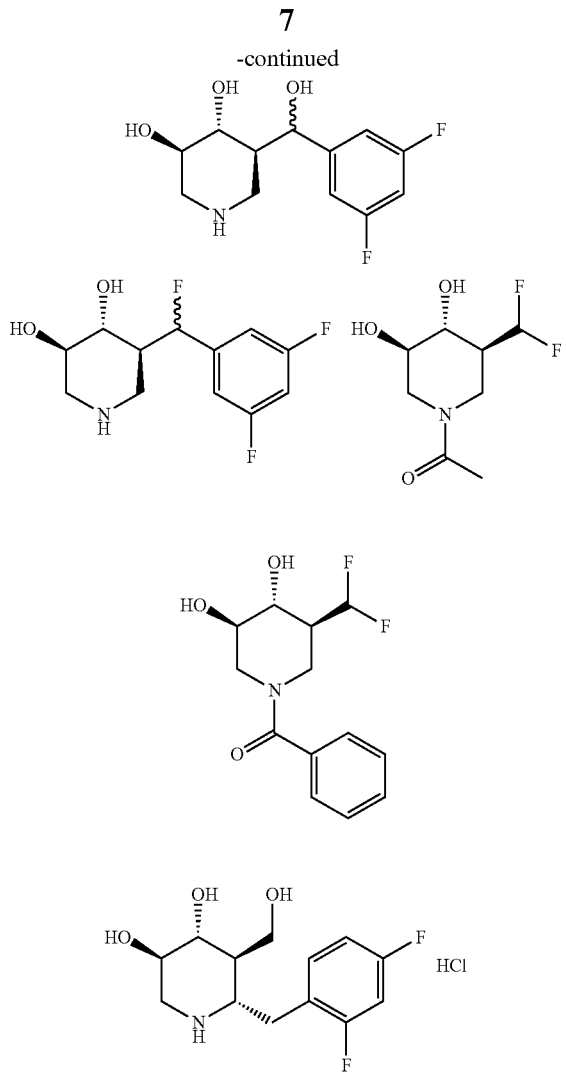

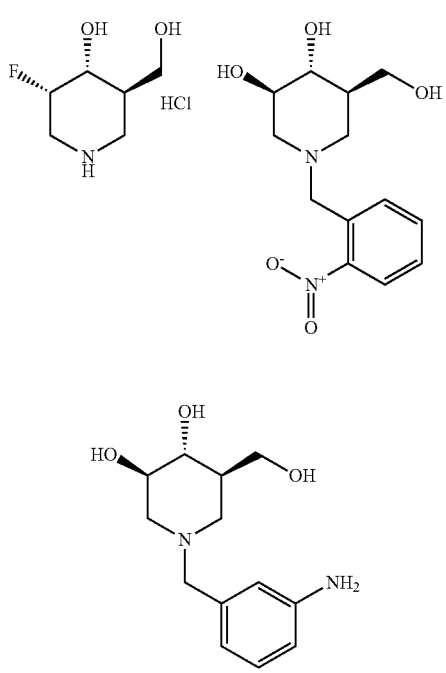

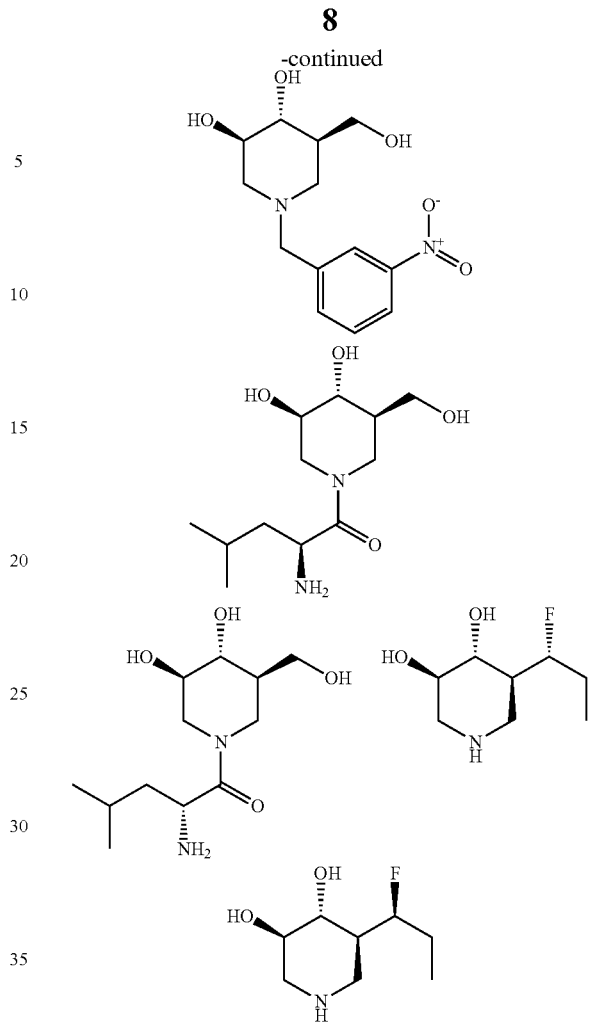

or a pharmaceutically acceptable salt, solvate, or prodrug thereof.

In one embodiment, the compound is (3R,4R,5S)-5-(difluoromethyl)piperidine-3,4-diol, (3R,4R,5S)-5-(1-fluoroethyl)piperidine-3,4-diol, (3R,4R,5S)-5-benzylpiperidine-3,4-diol, or a pharmaceutically acceptable salt, solvate, or prodrug thereof. In one embodiment, the compound is (3R, 4R,5S)-5-(difluoromethyl)piperidine-3,4-diol, or a pharmaceutically acceptable salt, solvate, or prodrug thereof. In one embodiment, the compound is (3R,4R,5S)-5-(1-fluoroethyl) piperidine-3,4-diol, or a pharmaceutically acceptable salt, solvate, or prodrug thereof. In one embodiment, the compound is (3R,4R,5S)-5-benzylpiperidine-3,4-diol, or a pharmaceutically acceptable salt, solvate, or prodrug thereof.

In one embodiment, the degenerative disorder is a synucleinopathy. In one embodiment, the degenerative disorder is characterized by Lewy bodies. In one embodiment, the degenerative disorder is Parkinson's disease, dementia with Lewy bodies, multiple system atrophy or Alzheimer's disease. In one embodiment, the degenerative disorder is associated with aggregation of at least one protein. In one embodiment, the degenerative disorder is associated with aggregation of alpha-synuclein. In one embodiment, the degenerative disorder is associated with aggregation of non-Abeta component. In one embodiment, the degenerative disorder is associated with accumulation of at least one glycolipid. In one embodiment, the degenerative disorder is associated with accumulation of at least one glycosphingolipid. In one embodiment, the degenerative disorder is associated with accumulation of glucocerebroside. In one embodiment, the degenerative disorder is associated with a mutation in glucocerebrosidase. In one embodiment, the method further comprises administering an effective amount of at least one other therapeutic agent. In one embodiment, at least one other therapeutic agent is levodopa, an anticholinergic, a catechol-O-methyl transferase inhibitor, a dopamine receptor agonist, a monoamine oxidase inhibitor, a peripheral decarboxylase inhibitor, or an anti-inflammatory agent.

The present invention also provides methods for preventing and/or treating Parkinson's disease in a patient at risk for developing or diagnosed with the same, which comprises administering to the patient in need thereof an effective amount of any of the aforementioned compounds, or a pharmaceutically acceptable salt, solvate, or prodrug thereof, or any combination of two or more thereof.

In one embodiment, the method comprises administering the compound (3R,4R,5S)-5-(difluoromethyl)piperidine-3, 4-diol, (3R,4R,5S)-5-(1-fluoroethyl)piperidine-3,4-diol, (3R,4R,5S)-5-benzylpiperidine-3,4-diol, or a pharmaceutically acceptable salt, solvate, or prodrug thereof. In one embodiment, the method comprises administering the compound (3R,4R,5S)-5-(difluoromethyl)piperidine-3,4-diol, or a pharmaceutically acceptable salt, solvate, or prodrug thereof. In one embodiment, the method comprises administering the compound (3R,4R,5S)-5-(1-fluoroethyl)piperidine-3,4-diol, or a pharmaceutically acceptable salt, solvate, or prodrug thereof. In one embodiment, the method comprises administering the compound (3R,4R,5S)-5-benzylpiperidine-3,4-diol, or a pharmaceutically acceptable salt, solvate, or prodrug thereof.

In one embodiment, the method comprises administering an effective amount of at least one other therapeutic agent. In one embodiment, at least one other therapeutic agent is levodopa, an anticholinergic, a catechol-β-methyl transferase inhibitor, a dopamine receptor agonist, a monoamine oxidase inhibitor, a peripheral decarboxylase inhibitor, or an anti-inflammatory agent.

The present invention also provides kits comprising:
a container having an effective amount of any of the compounds of the present invention, alone or in combination; and
instructions for using the same to prevent and/or treat a degenerative disorder of the central nervous system.

In one embodiment, the degenerative disorder of the central nervous system is Parkinson's disease. In one embodiment, the degenerative disorder of the central nervous system is Alzheimer's disease.

DETAILED DESCRIPTION OF THE INVENTION

As used herein the following terms shall have the definitions set forth below.

As used herein, the phrase "degenerative disorder of the central nervous system" means any disorder associated with the premature degeneration of any component of the central nervous system, such as neurons, myelin sheaths or axons. Such disorders include but are not limited to multi-infarct dementia, Huntington's disease, Pick's disease, amyotrophic lateral sclerosis, Creutzfeldt-Jakob's disease, frontal-lobe degeneration, corticobasal degeneration, progressive supranuclear palsy, Parkinson's disease, dementia with Lewy bodies, multiple system atrophy or Alzheimer's disease.

As used herein the term "treating" means to ameliorate one or more symptoms associated with the referenced disorder.

As used herein, the term "preventing" means to mitigate a symptom of the referenced disorder.

As used herein the phrase "an effective amount" means an amount effective to prevent and/or treat a patient at risk for developing or diagnosed with the referenced disorder, and thus producing the desired therapeutic effect.

As used herein the term "patient" means a mammal (e.g., a human).

Listed below are chemical definitions of various terms used to describe this invention. These definitions apply to the terms as they are used throughout this specification, unless otherwise limited in specific instances, either individually or as part of a larger group.

The term "alkyl" refers to straight or branched chain unsubstituted hydrocarbon groups of 1 to 20 carbon atoms, preferably 1 to 8 carbon atoms, more preferably 1 to 6 carbon atoms. The expression "lower alkyl" refers to unsubstituted alkyl groups of 1 to 4 carbon atoms.

The term "substituted alkyl" refers to an alkyl group substituted by, for example, one to four substituents, such as, halo, hydroxy, alkoxy, oxo, alkanoyl, aryloxy, alkanoyloxy, amino, alkylamino, arylamino, aralkylamino, disubstituted amines in which the 2 amino substituents are selected from alkyl, aryl or aralkyl; alkanoylamino, aroylamino, aralkanoylamino, substituted alkanoylamino, substituted arylamino, substituted aralkanoylamino, thiol, alkylthio, arylthio, aralkylthio, alkylthiono, arylthiono, aralkylthiono, alkylsulfonyl, arylsulfonyl, aralkylsulfonyl, sulfonamido, e.g. $SO_2NH_2$, substituted sulfonamido, nitro, cyano, carboxy, carbamyl, e.g. $CONH_2$, substituted carbamyl e.g. CONHalkyl, CONHaryl, CONHaralkyl or cases where there are two substituents on the nitrogen selected from alkyl, aryl or aralkyl; alkoxycarbonyl, aryl, substituted aryl, guanidino and heterocycles, such as, indolyl, imidazolyl, furyl, thienyl, thiazolyl, pyrrolidyl, pyridyl, pyrimidyl and the like. Where noted above where the substituent is further substituted it will be with alkyl, alkoxy, aryl or aralkyl.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "aralkyl" refers to an aryl group bonded directly through an alkyl group, such as benzyl. Similarly, the term "alkylaryl" refers to an alkyl group bonded directly through an aryl group, such as methylbenzyl.

The term "substituted aryl" refers to an aryl group substituted by, for example, one to four substituents such as alkyl, substituted alkyl, halo, trifluoromethoxy, trifluoromethyl, hydroxy, alkoxy, alkanoyl, alkanoyloxy, amino, alkylamino, aralkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkysulfonyl, sulfonamido, aryloxy and the like. The substituent may be further substituted by hydroxy, alkyl, alkoxy, aryl, substituted aryl, substituted alkyl or aralkyl.

The term "heteroaryl" refers to an optionally substituted, aromatic group for example, which is a 4 to 7 membered monocyclic, 7 to 11 membered bicyclic, or 10 to 15 membered tricyclic ring system, which has at least one heteroatom and at least one carbon atom-containing ring, for example, pyridine, tetrazole, indazole.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "substituted alkenyl" refers to an alkenyl group substituted by, for example, one to two substituents, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino, indolyl, imidazolyl, furyl, thienyl, thiazolyl, pyrrolidyl, pyridyl, pyrimidyl and the like.

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

The term "substituted alkynyl" refers to an alkynyl group substituted by, for example, a substituent, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclo, e.g. imidazolyl, furyl, thienyl, thiazolyl, pyrrolidyl, pyridyl, pyrimidyl and the like.

The term "cycloalkyl" refers to an optionally substituted, saturated cyclic hydrocarbon ring systems, preferably containing 1 to 3 rings and 3 to 7 carbons per ring which may be further fused with an unsaturated C3-C7 carbocylic ring. Exemplary groups include cyclopropyl, cyclobutyl, cyclopentyl, cyclohexyl, cycloheptyl, cycloctyl, cyclodecyl, cyclododecyl, and adamantyl. Exemplary substituents include one or more alkyl groups as described above, or one or more groups described above as alkyl substituents.

The terms "heterocycle", "heterocyclic" and "heterocyclo" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, dioxanyl, isothiazolidinyl, thietanyl, thiiranyl, triazinyl, and triazolyl, and the like.

Exemplary bicyclic hetrocyclic groups include 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Exemplary substituents include one or more alkyl or aralkyl groups as described above or one or more groups described above as alkyl substituents.

Also included are smaller heterocyclos, such as, epoxides and aziridines.

The term "heteroatoms" shall include oxygen, sulfur and nitrogen.

Parkinson's disease may be diagnosed in patients according to the United Kingdom Parkinson's Disease Society brain-bank clinical diagnostic criteria (see, Hughes et al., Accuracy of clinical diagnosis of idiopathic Parkinson's disease: a clinico-pathological study of 100 cases. J Neurol Neurosurg Psychiatry 1992; 55:181-184) and/or the criteria described by Gelb et al., Diagnostic Criteria for Parkinson's Disease. *Arch Neurol.* 1999; 56(1):33-39. Likewise, the severity of Parkinson's disease may be ascertained using the Unified Parkinson's Disease Rating Scale. See, e.g., Fahn and Elton, Members of the Unified Parkinson's Disease Rating Scale Development Committee. Unified Parkinson's Disease Rating Scale. In: Fahn et al., Recent developments in Parkinson's disease. New York: Macmillan, 1987: 153-163.

Alzheimer's disease may be diagnosed in patients according to the criteria for dementia of the Alzheimer's type of the Diagnostic and Statistical Manual of Mental Disorders, 4$^{th}$ ed.: DSM-IV. Washington, D.C.: American Psychiatric Association, 1994. Likewise, the criteria for probable Alzheimer's disease may be ascertained based on criteria of the National Institute of Neurological and Communicative Disorders and Stroke and the Alzheimer's Disease and Related Disorders Association. See also, McKhann et al., Clinical diagnosis of Alzheimer's disease: report of the NINCDS-ADRDA work group under the auspices of Department of Health and Human Services Task Force on Alzheimer's Disease. Neurology 1984; 34:939-944.

Multiple system atrophy (MSA) is characterized by glial cytoplasmic inclusion bodies (also known as Papp-Lantos bodies) in the movement, balance and automatic control centers of the brain. The most common first sign of MSA is the appearance of an "akinetic-rigid syndrome" (i.e., slowness of initiation of movement resembling Parkinson's disease) found in 62% at first presentation. Other common signs at onset include problems with balance (found in 22%), followed by genito-urinary problems (9%). For men, the first sign can be erectile dysfunction (unable to achieve or sustain an erection). Both men and women often experience problems with their bladders including urgency, frequency, incomplete bladder emptying or an inability to pass urine (retention). About 1 in 5 MSA patients will suffer a fall in their first year of disease. As the disease progresses three groups of symptoms predominate. These are: (i) parkinsonism (slow, stiff movement, writing becomes small and spidery); (ii) cerebellar dysfunction (difficulty coordinating movement and balance); and (iii) autonomic dysfunction (impaired automatic body functions) including: postural or orthostatic hypotension, resulting in dizziness or fainting upon standing up, urinary incontinence, impotence; constipation; dry mouth and skin; trouble regulating body temperature due to abnormal sweating; abnormal breathing during sleep. Notably, not all of these symptoms are experienced by all patients.

Dementia with Lewy bodies (DLB) is one of the most common types of progressive dementia. The central feature of DLB is progressive cognitive decline, combined with three additional defining features: (1) pronounced "fluctuations" in alertness and attention, such as frequent drowsiness, lethargy, lengthy periods of time spent staring into space, or disorganized speech; (2) recurrent visual hallucinations, and (3) parkinsonian motor symptoms, such as rigidity and the loss of spontaneous movement. People may also suffer from depression. The symptoms of DLB are caused by the build-up of Lewy bodies—accumulated bits of alpha-synuclein protein—inside the nuclei of neurons in areas of the brain that control particular aspects of memory and motor control. Researchers don't know exactly why alpha-synuclein accumulates into Lewy bodies or how Lewy bodies cause the symptoms of DLB, but they do know that alpha-synuclein accumulation is also linked to Parkinson's disease, multiple system atrophy, and several other disorders, which are referred to as the "synucleinopathies." The similarity of symptoms between DLB and Parkinson's disease, and between DLB and Alzheimer's disease, can often make it difficult for a doctor to make a definitive diagnosis. In addition, Lewy bodies are often also found in the brains of people with Parkinson's and Alzheimer's diseases. These findings suggest that either DLB is related to these other causes of dementia or that an individual can have both diseases at the same time. DLB usually occurs sporadically, in people with no known family history of the disease. However, rare familial cases have occasionally been reported.

Compounds

Novel compounds of the present invention are provided below:

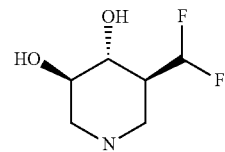

(3R, 4R, 5S)-5-(difluoromethyl)piperidine-3,4-diol

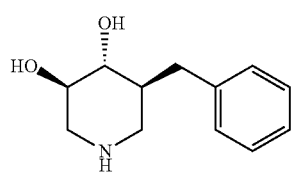

(3R, 4R, 5S)-5-benzylpiperidine-3,4-diol

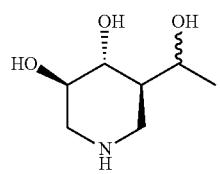

(3R, 4R, 5R)-5-(1-hydroxyethyl)piperidine-3,4-diol

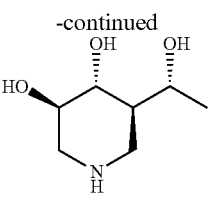

(3R, 4R, 5R)-5-(1-hydroxyethyl)piperidine-3,4-diol (stereoisomer A)

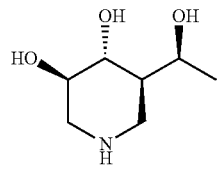

(3R, 4R, 5R)-5-(1-hydroxyethyl)piperidine-3,4-diol (stereoisomer B)

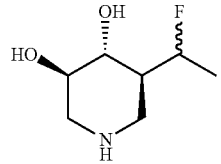

(3R, 4R, 5S)-5-(1-fluoroethyl)piperidine-3,4-diol

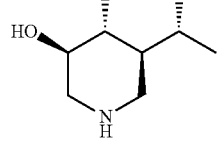

(3R, 4R, 5S)-5-(1-fluoroethyl)piperidine-3,4-diol (stereoisomer A)

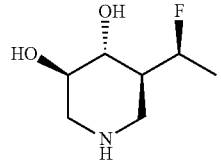

(3R, 4R, 5S)-5-(1-fluoroethyl)piperidine-3,4-diol (stereoisomer B)

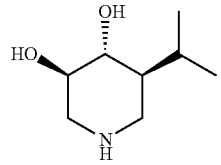

(3R, 4R, 5S)-5-ethylpiperidine-3,4-diol

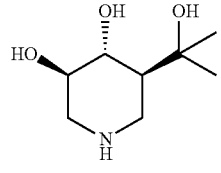

(3R, 4R, 5S)-5-isopropylpiperidine-3,4-diol (3R, 4R, 5S)-5-(2-hydroxypropan-2-yl)piperidine-3,4-diol -continued

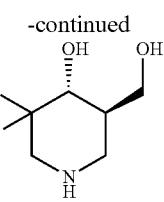

(4R, 5R)-3,3-difluoro-5-(hydroxymethyl)
piperidin-4-ol

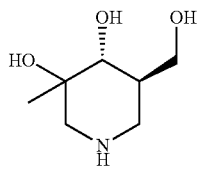

(4R, 5R)-5-(hydroxymethyl)-3-methylpiperidine-
3,4-diol

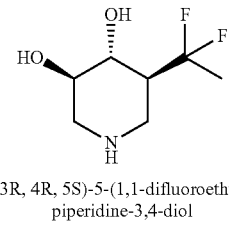 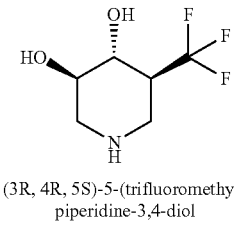

(3R, 4R, 5S)-5-(1,1-difluoroethyl)
piperidine-3,4-diol (3R, 4R, 5S)-5-(trifluoromethyl)
piperidine-3,4-diol

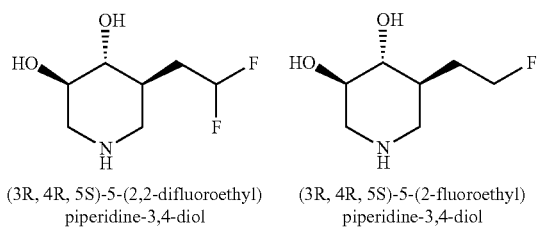

(3R, 4R, 5S)-5-(2,2-difluoroethyl)
piperidine-3,4-diol (3R, 4R, 5S)-5-(2-fluoroethyl)
piperidine-3,4-diol

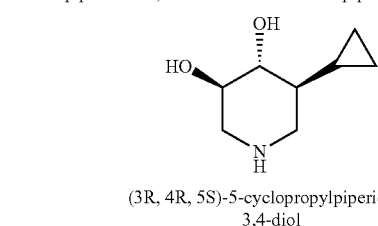

(3R, 4R, 5S)-5-cyclopropylpiperidine-
3,4-diol

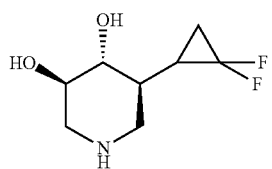

(3R, 4R, 5S)-5-(2,2-difluorocyclopropyl)
piperidine-3,4-diol

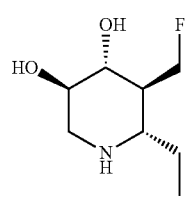

(3R, 4R, 5S, 6S)-6-ethyl-5-(fluoromethyl)
piperidine-3,4-diol

-continued

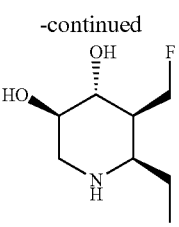

(3R, 4R, 5S, 6R)-6-ethyl-5-(fluoromethyl)
piperidine-3,4-diol

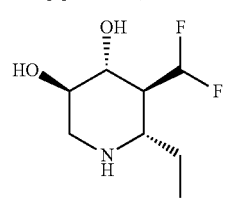

(3R, 4R, 5S, 6S)-5-(difluoromethyl)-6-
ethylpiperidine-3,4-diol

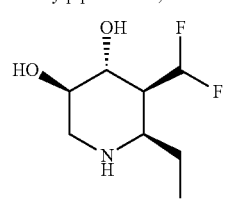

(3R, 4R, 5S, 6R)-5-(difluoromethyl)-6-
ethylpiperidine-3,4-diol

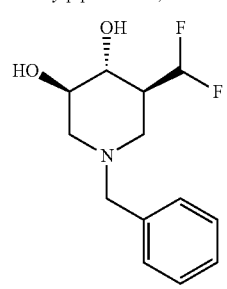

(3R, 4R, 5S)-1-benzyl-5-(difluoromethyl)
piperidine-3,4-diol

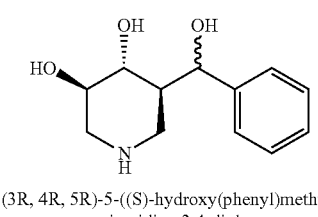

(3R, 4R, 5R)-5-((S)-hydroxy(phenyl)methyl)
piperidine-3,4-diol

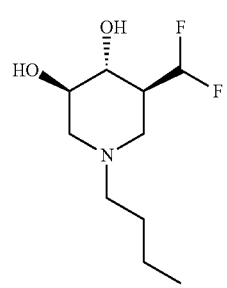

(3R, 4R, 5S)-1-butyl-5-(difluoromethyl)
piperidine-3,4-diol

-continued

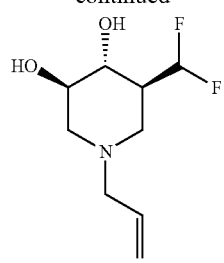

(3R, 4R, 5S)-1-allyl-5-(difluoromethyl)
piperidine-3,4-diol

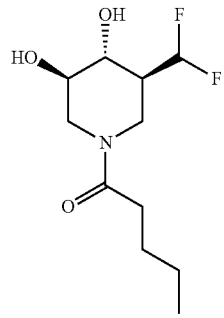

1-((3S, 4R, 5R)-3-(difluoromethyl)-4,5-
dihydroxypiperidin-1-yl)pentan-1-one

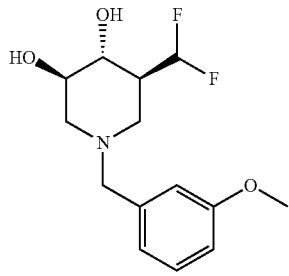

(3R, 4R, 5S)-5-(difluoromethyl)-1-(3-
methoxybenzyl)piperidine-3,4-diol

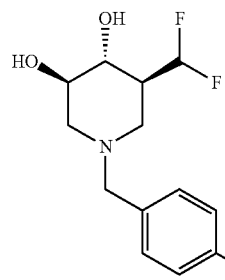

(3R, 4R, 5S)-5-(difluoromethyl)-1-(4-
methylbenzyl)piperidine-3,4-diol

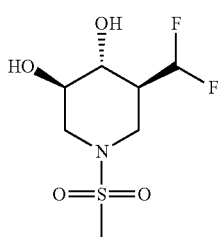

(3R, 4R, 5S)-5-(difluoromethyl)-1-
(methylsulfonyl)piperidine-3,4-diol (3R, 4R, 5S)-5-(difluoromethyl)-1-
(4-fluorobenzyl)piperidine-3,4-diol -continued

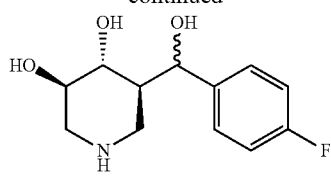

(3R, 4R, 5R)-5-((4-fluorophenyl)(hydroxy)
methyl)piperidine-3,4-diol

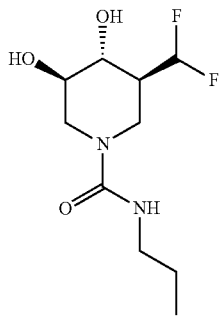

(3S, 4R, 5R)-3-(difluoromethyl)-4,5-
dihydroxy-N-propylpiperidine-1-carboxamide

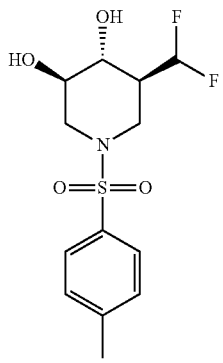

(3R, 4R, 5S)-5-(difluoromethyl)-1-tosylpiperidine-
3,4-diol

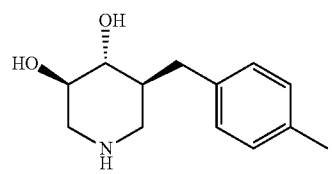

(3R, 4R, 5S)-5-(4-methylbenzyl)piperidine-
3,4-diol

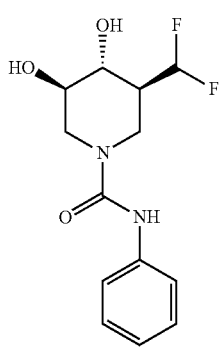

(3S, 4R, 5R)-3-(difluoromethyl)-4,5-
dihydroxy-N-phenylpiperidine-1-carboxamide

-continued

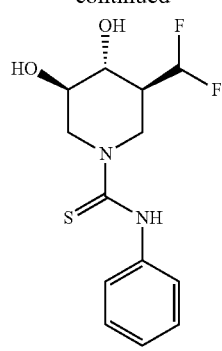

(3S, 4R, 5R)-3-(difluoromethyl)-4,5-
dihydroxy-N-phenylpiperidine-1-carbothioamide

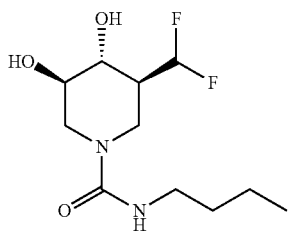

(3S, 4R, 5R)-N-butyl-3-(difluoromethyl)-4,5-
dihydroxypiperidine-1-carboxamide

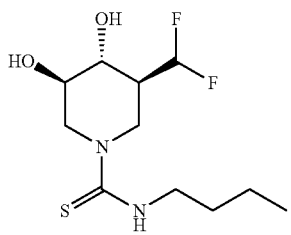

(3S, 4R, 5R)-N-butyl-3-(difluoromethyl)-4,5-
dihydroxypiperidine-1-carbothioamide

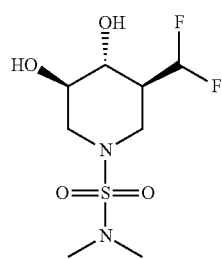

(3S, 4R, 5R)-3-(difluoromethyl)-4,5-
dihydroxy-N,N-dimethylpiperidine-1-sulfonamide

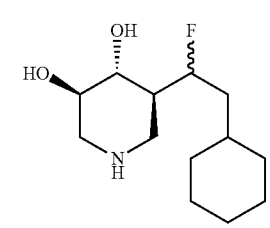

(3R, 4R, 5R)-5-(2-cyclohexyl-1-
hydroxyethyl)piperidine-3,4-diol (3R, 4R, 5S)-5-(2-cyclohexyl-1-
fluoroethyl)piperidine-3,4-diol -continued

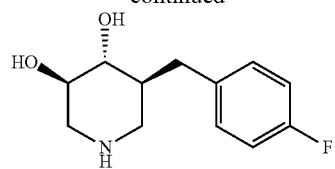

(3R, 4R, 5S)-5-(4-fluorobenzyl)
piperidine-3,4-diol

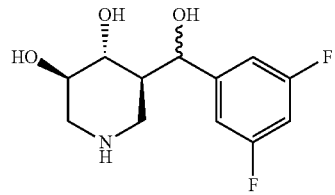

(3R, 4R, 5R)-5-((3,5-difluorophenyl)
(hydroxy)methyl)piperidine-3,4-diol

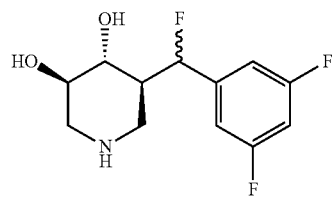

(3R, 4R, 5S)-5-((3,5-difluorophenyl)
fluoromethyl)piperidine-3,4-diol

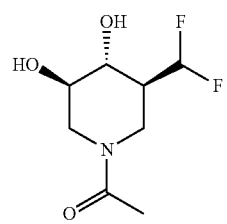

1-((3S, 4R, 5R)-3-(difluoromethyl)-4,5-
dihydroxypiperidin-1-yl)ethanone

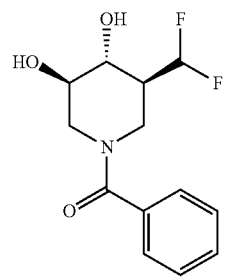

((3S, 4R, 5R)-3-(difluoromethyl)-4,5-
dihydroxypiperidin-1-yl)(phenyl)methanone

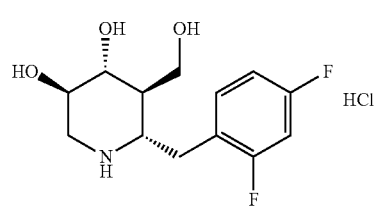

(3R, 4R, 5R, 6S)-6-(2,4-difluorobenzyl)-5-
(hydroxymethyl)piperidine-3,4-diol hydrochloride

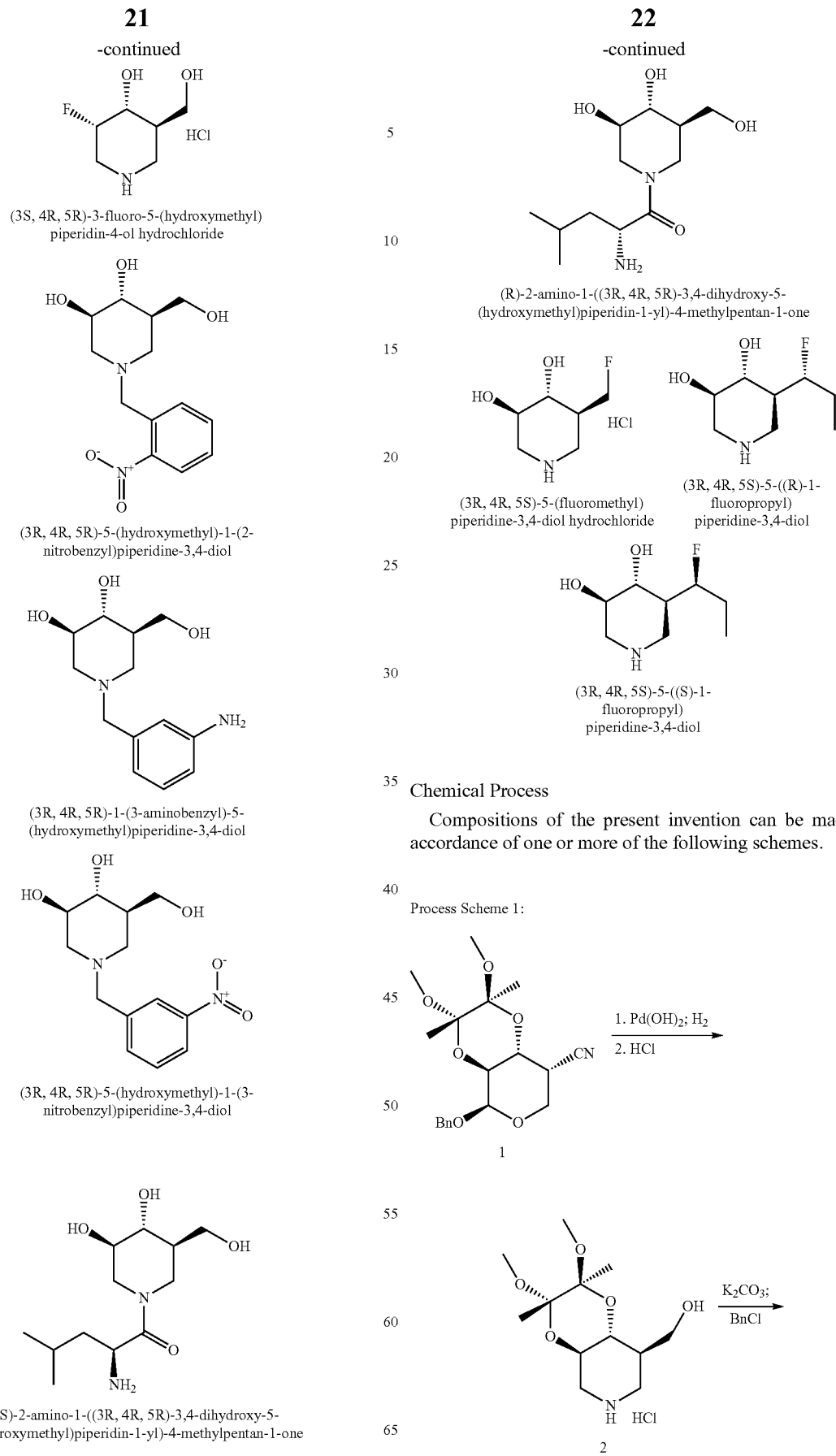

-continued

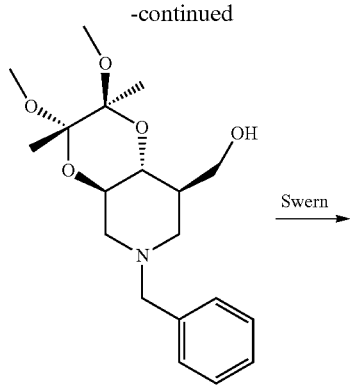

3

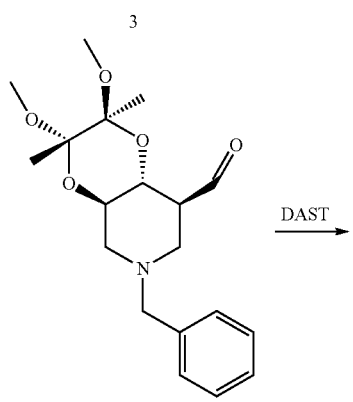

4

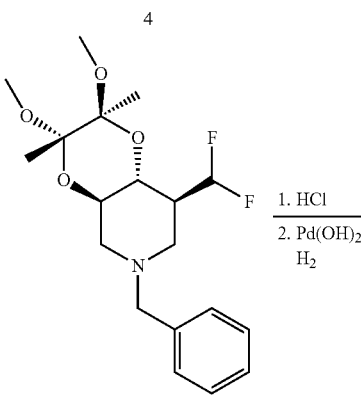

5

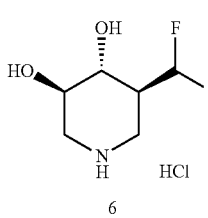

6

((2S,3S,4aR,8R,8aR)-2,3-Dimethoxy-2,3-dimethyloctahydro-[1,4]dioxino[2,3-c]pyridin-8-yl)methanol Hydrochloride (2)

A solution of 1 (20.0 g, 55.0 mmol) in MeOH (500 mL) was combined with Pd(OH)$_2$ (4-6 g) and ammonium formate (14 g, 220 mmol) and the mixture was heated at 50-55° C. Additional amounts (3×100.0 mmol) of ammonium formate were added over the next 8 hrs. After the final addition, the reaction mixture was further stirred and heated an additional 16 hrs at 50-55° C. The catalyst was removed by filtration and the filtrate was evaporated in vacuo. The crude product was dissolved in acetone (150 mL), filtered, and HCl in 2-PrOH was added. After seeding and then cooling in an ice bath, the product was collected as a white crystalline solid (11.0 g, 71%). 1H NMR (DMSO-d6) 9.45 (s, 2H), 4.80 (t, 1H, ex), 3.85 (m, 1H), 3.0-3.75 (m, 11H), 2.8 (q, 2H), 1.95 (m, 1H), 1.2 (2, 6H).

((2S,3S,4aR,8R,8aR)-6-Benzyl-2,3-dimethoxy-2,3-dimethyloctahydro-[1,4]dioxino[2,3-c]pyridin-8-yl) methanol (3)

To a solution of 2 (14.85 g, 50.0 mmol) in DMF (200 mL) was added K2CO3 (17.25 g, 125 mmol) and the mixture was stirred at 40° C. for about 4 hrs. At this point, BnCl (5.7 mL, 50.0 mmol) was added in one portion and the reaction was stirred at 40° C. overnight. The solvent was evaporated in vacuo and the residue was suspended in water (600 mL) and HCl was added to dissolve the residue. The solution was washed with Et2O and then basified with Na2CO3. The solution was extracted with EtOAc (2×) and the combined extracts were washed with water and then brine and then dried over MgSO4. The solution was filtered and the filtrate evaporated in vacuo to give the title compound (17.2 g, >95%) as a colorless to very pale yellow viscous oil which was used without further purification. 1H NMR (CDCl3) 7.3 (m, 5H), 3.6-3.8 (m, 2H), 3.5 (s, 3H), 3.4 (t, 1H), 3.26 (s, 3H), 3.268 (s, 3H), 2.9 (m, 2H), 2.2 (br s, 1H), 2.05 (m, 1H), 1.85 (t, 1H), 1.28 (s, 3H), 1.26 (s, 3H).

((2S,3S,4aR,8R,8aR)-6-Benzyl-2,3-dimethoxy-2,3-dimethyloctahydro-[1,4]dioxino[2,3-c]pyridin-8-yl) carboxaldehyde (General Procedure A) (4)

To a solution of DMSO (7.3 g, 96.9 mmol) in CH2Cl2 (150 mL) cooled to −78° C. was added a solution of oxalyl chloride (6.1 mL, 72.8 mmol) in CH$_2$Cl$_2$ dropwise. After the addition was complete the reaction mixture was stirred for an additional 30 min at which point a solution of 3 (17.0 g, 48.4 mmol) in CH$_2$Cl$_2$ was added dropwise. After addition was complete, the reaction was stirred for 1 hr at −78° C. and then diisopropylethylamine (34.4 mL, 193 mmol) was added dropwise. After this addition was complete, the cooling bath was removed and the reaction mixture was allowed to warm to 0° C. when saturated NaHCO3 was added. The mixture was diluted with some additional CH$_2$Cl$_2$ and then the organic layer was separated and dried over MgSO4. After filtering, the solvent was evaporated in vacuo and the crude product was purified by silica gel chromatography (Hex/EtOAc) to give the title compound (12.7 g, 75%) as a viscous oil. 1H NMR (CDCl3) 9.73 (s, 1H), 7.2 (m, 5H), 3.75 (m, 2H), 3.5 (q, 2H), 3.2 (2 s, 6H), 2.7-3.0 (m, 3H), 2.05 (m, 2H), 1.25 (2 s, 6H).

((2S,3S,4aR,8S,8aR)-6-Benzyl-8,8-difluoromethyl-2,3-dimethoxy-2,3-dimethyloctahydro-[1,4]dioxino [2,3-c]pyridine Hydrochloride (General Procedure B) (5)

To a solution of DAST (1.4 mL, 10.3 mmol) in CH2Cl2 (50 mL) cooled to −15° C. was added a solution of 4 (2.4 g, 6.9 mmol) dropwise. After 10 minutes, the ice bath was removed and the reaction was stirred at room temperature overnight. At this point the reaction mixture was again cooled in an ice bath and the reaction was quenched by addition of saturated NaHCO3 (dropwise at first since this does produce a slight exotherm). The organic layer was separated and dried over Na2SO4, filtered and the solvent was evaporated in vacuo to give a yellow oil. The residue was purified by chromatography on silica gel (Hex/EtOAc) to give the title compound (1.6 g, 62%) as a colorless oil. 1H NMR (CDCl3) 7.2 (m, 5H), 6.0 (dt, 1H), 3.75 (m, 1H), 3.55 (m, 3H), 3.2 (2 s, 6H), 2.95 (m, 1H), 2.85 (m, 1H), 2.3 (m, 2H), 1.5 (br s, 1H), 1.2 (2 s, 6H).

(3R,4R,5S)-5-(Difluoromethyl)piperidine 3,4-diol Hydrochloride (General Procedure C) (6)

Compound 5 (1.6 g, 4.3 mmol) was heated at reflux in a mixture of EtOH/H2O/HCl (40 mL/40 mL/5 mL) and the reaction monitored by HPLC until the starting material could no longer be detected. The solvent was evaporated in vacuo and then co-evaporated 2× with EtOH. The residue was dissolved in MeOH and hydrogenated over Pd(OH)2. When complete, the catalyst was removed by filtration and the filtrate evaporated in vacuo. The residue was recrystallized from EtOH (50 mL) to the title compound (0.55 g, 66%) as a white solid (mp 168-170° C.). 1H NMR (D2O) 6.15 (dt, 1H), 4.3-4.8 (m, 2H), 3.0 (t, 1H), 2.85 (t, 1H), 2.3 (m, 1H).

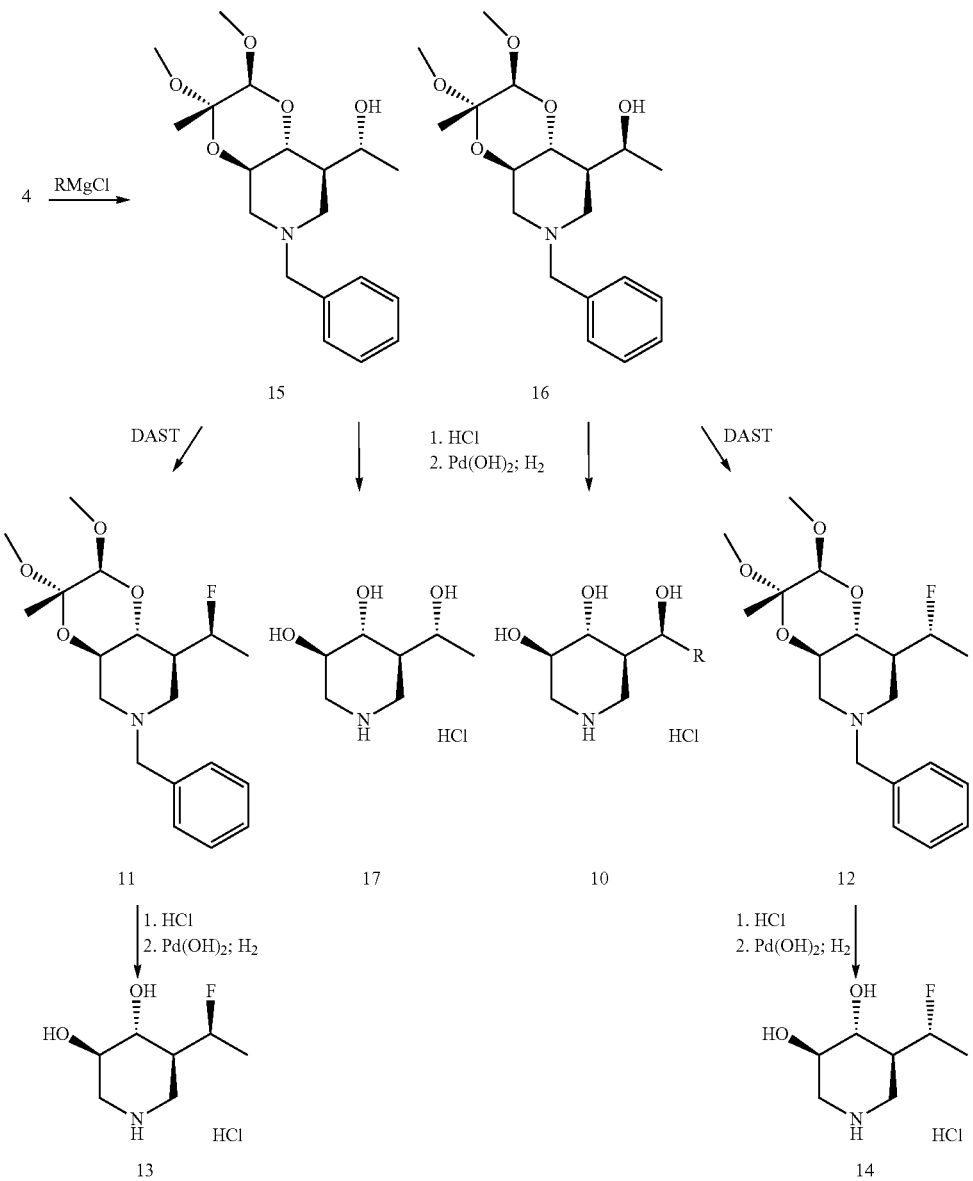

(R) and(S)-1-((2S,3S,4aR,8R,8aR)-6-Benzyl-2,3-dimethoxy-2,3-dimethyloctahydro-[1,4]dioxino[2,3-c]pyridin-8-yl)ethanol General Procedure D (15/16)

To a solution of 4 (7.0 g, 20.0 mmol) in dry THF (100 mL) was added MeMgBr (20.0 mL, 1.4 M in 3:1 THF/toluene) and the reaction was stirred overnight at room temperature. The reaction was quenched with saturated NH4Cl and the mixture was extracted with EtOAc (2×). The combined extracts were washed with brine, dried over Na2SO4 and the filtrate was evaporated in vacuo. The residue was purified by silica gel chromatography (hexane/2-PrOH) to give the major isomer (15) (1.6 g, 24.6%). 1H NMR (CDCl3). 7.3 (m, 5H), 4.15 (m, 1H), 3.5-3.9 (m, 3H), 3.3 (2 s, 6H), 2.85 (m, 2H), 2.0 (2 m, 4H), 1.3 (2 s, 6H), 1.2 (d, 3H). The minor isomer (16) was also isolated (0.55 g, 7.5%) 7.3 (m, 5H), 3.75 (m, 2H), 3.5 (m, 2H), 3.2 (2 s, 6H), 2.8 (m, 2H), 2.0 (t, 1H), 1.75 (m, 2H), 1.2 (2 s, 6H), 1.0 (d, 3H).

(3R,4R,5R)-5((R)-1-Hydroxyethyl)piperidine 3,4-diol (17)

Compound 15 (0.55 g, 1.5 mmol) was stirred in a mixture of 9/1 TFA:H2O (20 mL) until the starting material could no longer be detected by HPLC. The volatiles were removed and the residue was co-evaporated 2-3× with EtOH and then dissolved in EtOH and treated with solid K2CO3. After filtering the solid, the filtrate was evaporated in vacuo, and the residue was converted to an HCl salt and hydrogenated over Pd(OH)2. The catalyst was filtered and the filtrate evaporated in vacuo. The crude product was purified using an ion exchange resin (Dowex 50WX8-200) eluting with 0.1 N NH4OH. The appropriate fractions were combined and lyophilized to give the title compound (0.12 g, 50%). 1H NMR (D2O) 4.2 (q, 1H), 3.65 (m, 1H), 3.45 (m, 3H), 2.8 (m, 2H), 1.65 (m, 1H), 1.15 (d, 3H).

(3R,4R,5R)-5((S)-1-Hydroxyethyl)piperidine 3,4-diol (10)

Compound 16 (0.34 g, 0.93 mmol) was deprotected as described above to give the title compound (0.11 g, 75%). 1H NMR (D2O) 4.15 (m, 2H), 3.5 (m, 1H), 3.35 (t, 1H), 3.15 (m, 2H), 1.8 (m, 1H), 1.1 (d, 3H).

((2S,3S,4aR,8R,8aR)-6-Benzyl-8(S)-(1-fluoroethyl)-2,3-dimethoxy-2,3-dimethyloctahydro-[1,4]dioxino[2,3-c]pyridine (11)

Compound 15 (1.8 g, 5.0 mmol) was fluorinated using General Procedure B. Silica gel chromatography (Hex/EtOAc) gave the title compound (0.42 g, 23%). 1H NMR (CDCl3) 7.25 (m, 5H), 4.7-4.9 (dq, 1H), 3.75 (m, 2H), 3.4 (m, 2H), 3.2 (2 s, 6H), 2.8 (m, 2H), 2.0 (m, 3H), 1.35 (dd, 3H), 1.2 (2 s, 6H).

(3R,4R,5R)-5((S)-1-Fluoroethyl)piperidine 3,4-diol Hydrochloride (13)

Compound 11 (0.42 g, 1.14 mmol) was deprotected as described in General Procedure C. After catalyst was removed, the filtrate was evaporated in vacuo and then co-evaporated with EtOH (2×). The resulting residue was triturated with acetone to give the title compound (0.20 g, 88%) as a white solid. 1H NMR (DMSO-d6) 9.0 (br s, 2H), 5.6 (d, 1H, ex), 5.4 (d, 1H, ex), 5.0-5.2 (dq, 1H), 3.55 (m, 1H), 3.2 (m, 2H), 2.9 (t, 1H), 2.7 (t, 1H), 2.2 (m, 1H), 1.3 (dd, 3H).

((2S,3S,4aR,8R,8aR)-6-Benzyl-8(R)-(1-fluoroethyl)-2,3-dimethoxy-2,3-dimethyloctahydro-[1,4]dioxino[2,3-c]pyridine (12)

Compound 16 (0.55 g, 1.5 mmol) was fluorinated using General Procedure B to give the title compound (0.22 g, 40%). ¹H NMR (CDCl₃) 7.3 (m, 5H), 5.0 (dq, 1H), 3.8 (m, 1H), 3.5-3.75 (m, 3H), 3.3 (2 s, 6H), 3.0 (d, 1H), 2.9 (m, 1H), 2.1 (m, 2H), 1.85 (m, 1H), 1.3 (2 s, 6H).

(3R,4R,5R)-5((R)-(1-Fluoroethyl)piperidine 3,4-diol Hydrochloride (14)

Compound 12 (0.22 g, 0.6 mmol) was deprotected as described in General Procedure C. After catalyst was removed, the filtrate was evaporated in vacuo and then co-evaporated with EtOH (2×). The resulting residue was triturated with acetone to give the title compound (0.08 g, 67%) as a white solid. 1H NMR (D2O) 5.1 (dq, 1H), 3.5 (m, 4H), 2.8 (m, 2H), 1.8 (m, 1H), 1.3 (dd, 3H).

Process Scheme 2:

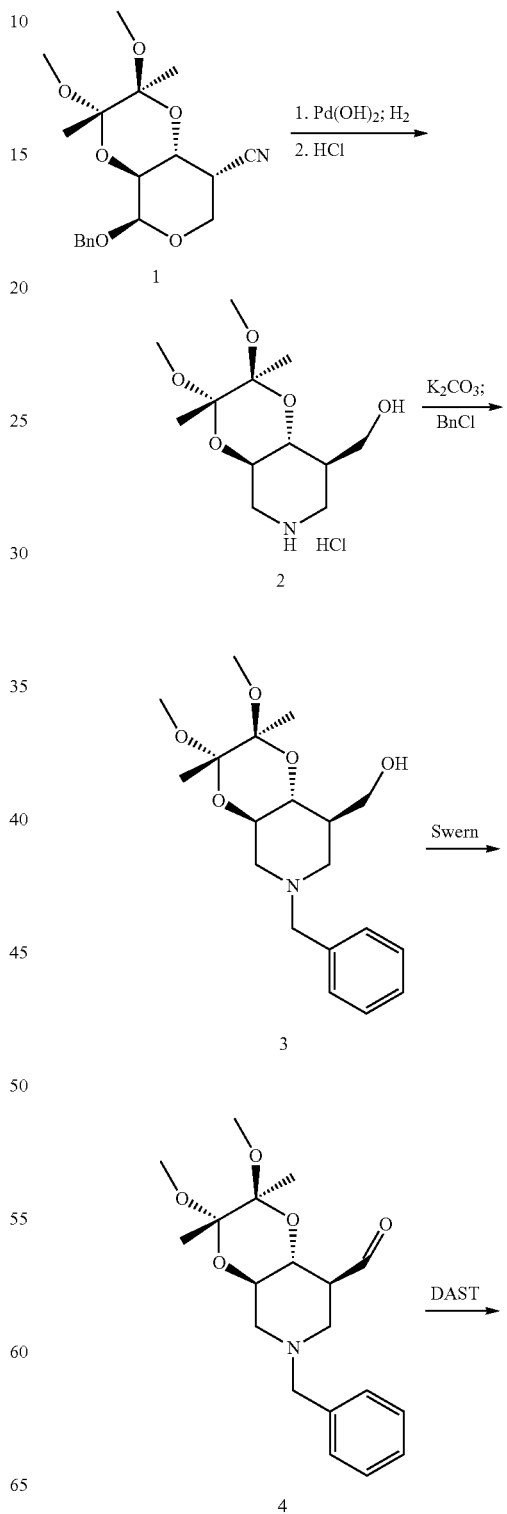

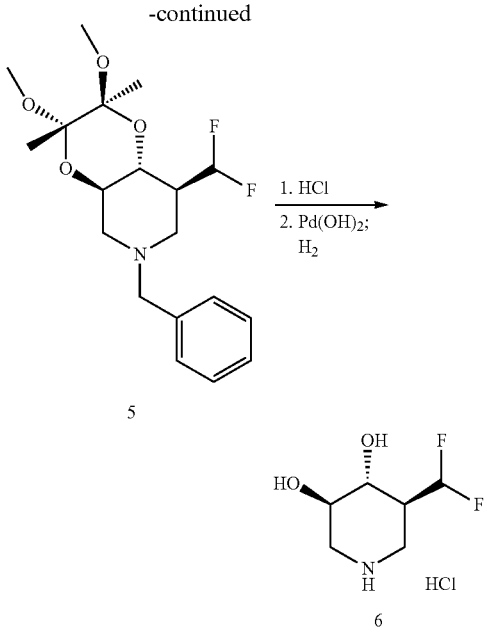

5

((2S,3S,4aR,8R,8aR)-2,3-Dimethoxy-2,3-dimethyloctahydro-[1,4]dioxino[2,3-c]pyridin-8-yl)methanol Hydrochloride (2)

A solution of 1 (20.0 g, 55.0 mmol) in MeOH (500 mL) was combined with Pd(OH)$_2$ (4-6 g) and ammonium formate (14 g, 220 mmol) and the mixture was heated at 50-55° C. Additional amounts (3×100.0 mmol) of ammonium formate were added over the next 8 hrs. After the final addition, the reaction mixture was further stirred and heated an additional 16 hrs at 50-55° C. The catalyst was removed by filtration and the filtrate was evaporated in vacuo. The crude product was dissolved in acetone (150 mL), filtered, and HCl in 2-PrOH was added. After seeding and then cooling in an ice bath, the product was collected as a white crystalline solid (11.0 g, 71%). $^1$H NMR (DMSO-d$_6$) 9.45 (s, 2H), 4.80 (t, 1H, ex), 3.85 (m, 1H), 3.0-3.75 (m, 11H), 2.8 (q, 2H), 1.95 (m, 1H), 1.2 (2, 6H).

((2S,3S,4aR,8R,8aR)-6-Benzyl-2,3-dimethoxy-2,3-dimethyloctahydro-[1,4]dioxino[2,3-c]pyridin-8-yl) methanol (3)

To a solution of 2 (14.85 g, 50.0 mmol) in DMF (200 mL) was added K$_2$CO$_3$ (17.25 g, 125 mmol) and the mixture was stirred at 40° C. for about 4 hrs. At this point, BnCl (5.7 mL, 50.0 mmol) was added in one portion and the reaction was stirred at 40° C. overnight. The solvent was evaporated in vacuo and the residue was suspended in water (600 mL) and HCl was added to dissolve the residue. The solution was washed with Et$_2$O and then basified with Na$_2$CO$_3$. The solution was extracted with EtOAc (2×) and the combined extracts were washed with water and then brine and then dried over MgSO$_4$. The solution was filtered and the filtrate evaporated in vacuo to give the title compound (17.2 g, >95%) as a colorless to very pale yellow viscous oil which was used without further purification. $^1$H NMR (CDCl$_3$) 7.3 (m, 5H), 3.6-3.8 (m, 2H), 3.5 (s, 3H), 3.4 (t, 1H), 3.26 (s, 3H), 3.268 (s, 3H), 2.9 (m, 2H), 2.2 (br s, 1H), 2.05 (m, 1H), 1.85 (t, 1H), 1.28 (s, 3H), 1.26 (s, 3H).

((2S,3S,4aR,8R,8aR)-6-Benzyl-2,3-dimethoxy-2,3-dimethyloctahydro-[1,4]dioxino[2,3-c]pyridin-8-yl) carboxaldehyde (General Procedure A) (4)

To a solution of DMSO (7.3 g, 96.9 mmol) in CH$_2$Cl$_2$ (150 mL) cooled to −78° C. was added a solution of oxalyl chloride (6.1 mL, 72.8 mmol) in CH$_2$Cl$_2$ dropwise. After the addition was complete the reaction mixture was stirred for an additional 30 min at which point a solution of 3 (17.0 g, 48.4 mmol) in CH$_2$Cl$_2$ was added dropwise. After addition was complete, the reaction was stirred for 1 hr at −78° C. and then diisopropylethylamine (34.4 mL, 193 mmol) was added dropwise. After this addition was complete, the cooling bath was removed and the reaction mixture was allowed to warm to 0° C. when saturated NaHCO$_3$ was added. The mixture was diluted with some additional CH$_2$Cl$_2$ and then the organic layer was separated and dried over MgSO$_4$. After filtering, the solvent was evaporated in vacuo and the crude product was purified by silica gel chromatography (Hex/EtOAc) to give the title compound (12.7 g, 75%) as a viscous oil. $^1$H NMR (CDCl$_3$) 9.73 (s, 1H), 7.2 (m, 5H), 3.75 (m, 2H), 3.5 (q, 2H), 3.2 (2 s, 6H), 2.7-3.0 (m, 3H), 2.05 (m, 2H), 1.25 (2 s, 6H).

((2S,3S,4aR,8S,8aR)-6-Benzyl-8,8-difluoromethyl-2,3-dimethoxy-2,3-dimethyloctahydro-[1,4]dioxino[2,3-c]pyridine Hydrochloride (General Procedure B) (5)

To a solution of DAST (1.4 mL, 10.3 mmol) in CH$_2$Cl$_2$ (50 mL) cooled to −15° C. was added a solution of 4 (2.4 g, 6.9 mmol) dropwise. After 10 minutes, the ice bath was removed and the reaction was stirred at room temperature overnight. At this point the reaction mixture was again cooled in an ice bath and the reaction was quenched by addition of saturated NaHCO$_3$ (dropwise at first since this does produce a slight exotherm). The organic layer was separated and dried over Na$_2$SO$_4$, filtered and the solvent was evaporated in vacuo to give a yellow oil. The residue was purified by chromatography on silica gel (Hex/EtOAc) to give the title compound (1.6 g, 62%) as a colorless oil. $^1$H NMR (CDCl$_3$) 7.2 (m, 5H), 6.0 (dt, 1H), 3.75 (m, 1H), 3.55 (m, 3H), 3.2 (2 s, 6H), 2.95 (m, 1H), 2.85 (m, 1H), 2.3 (m, 2H), 1.5 (br s, 1H), 1.2 (2 s, 6H).

(3R,4R,5S)-5-(Difluoromethyl)piperidine 3,4-diol Hydrochloride (General Procedure C) (6)

Compound 5 (1.6 g, 4.3 mmol) was heated at reflux in a mixture of EtOH/H$_2$O/HCl (40 mL/40 mL/5 mL) and the reaction monitored by HPLC until the starting material could no longer be detected. The solvent was evaporated in vacuo and then co-evaporated 2× with EtOH. The residue was dissolved in MeOH and hydrogenated over Pd(OH)$_2$. When complete, the catalyst was removed by filtration and the filtrate evaporated in vacuo. The residue was recrystallized from EtOH (50 mL) to the title compound (0.55 g, 66%) as a white solid (mp 168-170° C.). $^1$H NMR (D$_2$O) 6.15 (dt, 1H), 4.3-4.8 (m, 2H), 3.0 (t, 1H), 2.85 (t, 1H), 2.3 (m, 1H).

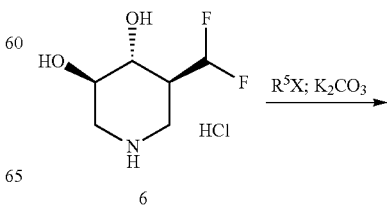

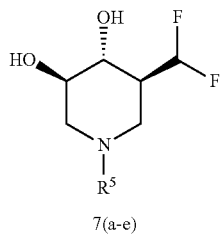

7(a-e)

(3R,4R,5S)-1.Butyl-5-(difluoromethyl)piperidine 3,4-diol (General Procedure D) (7a; R⁵=Bu)

A mixture of 6 (0.30 g, 1.4 mmol), K$_2$CO$_3$ (0.48 g, 3.5 mmol) and BuBr (0.20 g, 1.4 mmol) was combined in DMF (10 mL) and heated overnight at 60° C. The solvent was evaporated in vacuo and the residue was dissolved in EtOAc, washed with water and then brine and dried over Na$_2$SO$_4$. After filtration, the filtrate was evaporated in vacuo to give the crude product which was purified by chromatography (CH$_2$Cl$_2$/(9:1) MeOH/NH$_4$OH) to give the title compound (0.25 g, 80%) as a colorless syrup. MH$^+$=224. $^1$H NMR (DMSO-d$_6$) 6.2 (t, 1H, J=57 Hz), 5.13 (d, 1H, ex), 4.91 (d, 1H, ex), 3.3 (m, 1H), 3.1 (m, 1H), 2.9 (m, 2H), 2.3 (m, 2H), 1.95 (m, 2H), 1.75 (t, 1H), 1.2-1.5 (2 m, 4H), 0.9 (t, 3H).

(3R,4R,5S)-1.Allyl-5-(difluoromethyl)piperidine 3,4-diol (7b; R⁵=allyl)

Following General Procedure D using allyl bromide (0.17 g, 1.4 mmol) the tile compound was obtained as a white solid (0.22 g, 76%). MH$^+$=208. $^1$H NMR (DMSO-d$_6$) 6.2 (t, 1H, J=57 Hz), 5.8 (m, 1H), 5.2 (m, 3H), 4.92 (d, 1H), 3.3 (m, 1H), 3.1 (1H), 2.95 (d, 2H), 2.85 (d, 2H), 1.9 (br m, 2H), 1.75 (t, 1H).

(3R,4R,5S)-5-(Difluoromethyl)-1-(4-fluorobenzyl)piperidine 3,4-diol (7c; R⁵=4-fluorobenzyl)

Following General Procedure D except that reaction was run at room temperature and using 4-fluorobenzyl bromide (0.26 g, 1.4 mmol) the tile compound was obtained as a white solid (0.22 g, 56%). MH$^+$=276. $^1$H NMR (DMSO-d$_6$) 7.4 (m, 2H), 7.15 (m, 2H), 6.2 (t, 1H, J=57 Hz), 5.2 (d, 1H, ex), 4.9 (d, 1H, ex), 3.5 (q, 2H), 3.3 (m, 1H), 3.1 (m, 1H), 2.8 (m, 2H), 2.0 (m, 2H), 1.8 (t, 1H).

(3R,4R,5S)-5-(Difluoromethyl)-1-(4-methylbenzyl)piperidine 3,4-diol (7d; R⁵=4-methylbenzyl)

Following General Procedure D except that reaction was run at room temperature and using 4-methylbenzyl bromide (0.26 g, 1.4 mmol) the tile compound was obtained as a white solid (0.30, 81%). MH$^+$=272. $^1$H NMR (DMSO-d$_6$) 7.2 (m, 4H), 6.2 (t, 1H, J=57 Hz), 5.2 (d, 1H, ex), 4.9 (d, 1H, ex), 3.5 (q, 2H), 3.3 (1H), 3.05 (m, 1H), 2.8 (m, 2H), 2.5 (s, 3H), 1.95 (m, 2H), 1.8 (t, 1H).

(3R,4R,5S)-5-(Difluoromethyl)-1-(4-methoxylbenzyl)piperidine 3,4-diol (7e; R⁵=4-methoxylbenzyl)

Following General Procedure D except that reaction was run at room temperature and using 4-methoxylbenzyl chloride (0.26 g, 1.4 mmol) the tile compound was obtained as a colorless syrup (0.19 g, 49%). MH$^+$=288. $^1$H NMR (DMSO-d$_6$) 7.3 (m, 1H), 6.85 (m, 3H) 6.2 (t, 1H, J=57 Hz), 5.2 (d, 1H, ex), 4.9 (d, 1H, ex), 3.75 (s, 3H), 3.5 (q, 2H), 3.4 (m, 1H), 3.1 (m, 1H), 2.85 (m, 2H), 1.95 (m, 2H), 1.8 (t, 1H).

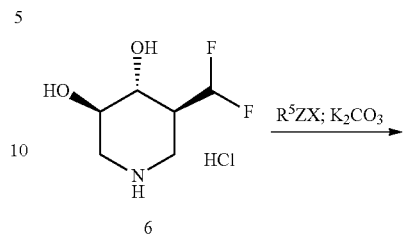

6

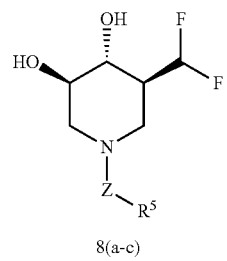

8(a-c)

1-((3S,4R,5R)-3-(Difluoromethyl)-4,5-dihydroxypiperidine-1-yl)pentane-1-one (8a; Z=CO; R⁵=butyl)

Following General Procedure D, except that the reaction was run at room temperature and using pentanoyl chloride (0.17 g, 1.4 mmol), the title compound was obtained as a white solid (0.26 g, 71%). MH$^+$=252. $^1$H NMR (DMSO-d$_6$) 5.9-6.5 (dt, 1H), 5.35 (m, 1H, ex), 5.25 (m, 1H), ex), 4.2 (dd, 1H), 3.75 (dd, 1H), 3.35 (m, 2H), 3.1 (m, 1H), 2.85 (m, 1H), 2.3 (t, 2H), 1.9 br m, 1H), 1.4 (m, 2H), 1.25 (m, 2H), 0.85 (t, 3H).

(3R,4R,5S)-5-(Difluoromethyl)-1-(methanesulfonyl)piperidine 3,4-diol (8b; Z=SO$_2$; R⁵=Me)

Following General Procedure D except that the reaction was run at room temperature and using methanesulfonyl chloride (0.16 g, 1.4 mmol), the title compound was obtained as a white solid (0.17 g, 51%). $^1$H NMR (DMSO-d$_6$) 6.2 (t, 1H, J=53 Hz), 5.43 (d, 1H, ex), 5.38 (d, 1H, ex), 3.2-3.7 (m, 4H), 2.95 (s, 3H), 2.85 (m, 1H), 2.7 (t, 1H), 2.1 (br s, 1H).

(3R,4R,5S)-5-(Difluoromethyl)-1-tosylpiperidine 3,4-diol (8b; Z=SO$_2$; R⁵=Ph)

Following General Procedure D except that the reaction was run at room temperature and using toluenesulfonyl chloride (0.26, 1.4 mmol), the title compound was obtained as a white solid (0.35 g, 67%). $^1$H NMR (DMSO-d$_6$) 7.6 (d, 2H), 7.45 (d, 2H), 6.25 (t, 1H, J=53 Hz), 5.4 (2d, 2H, ex), 3.3-3.55 (m, 4H), 3.2 (m, 1H), 2.5 (m, 3H), 2.4 (t, 1H), 2.1 (m, 1H).

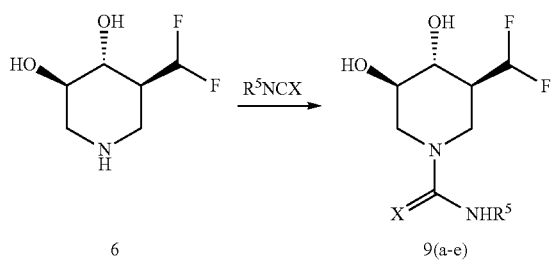

(3S,4R,5R)-3-(Difluoromethyl)-4,5-dihydroxy-N-propylpiperidine-1-carboxamide (General Procedure E) (9a; X=O; R⁵=propyl)

To a solution of 6 (free base) (0.29 g, 1.2 mmol) in dry DMF (5 mL), was added propyl isocyanate (0.10 g, 1.2 mmol) and the reaction was stirred at room temperature overnight. The solvent was evaporated in vacuo and the residue was purified by chromatography (CH$_2$Cl$_2$/MeOH) to give the title compound as a white solid (0.14 g, 48%). MH$^+$=253. $^1$H NMR (DMSO-d$_6$) 6.7 (t, 1H), 6.22 (t, 1H, J=53 Hz), 5.25 (d, 1H, ex), 5.15 (d, 1H, ex), 4.05 (d, 1H), 3.9 (d, 1H), 3.3 (m, 2H), 3.0 (q, 2H), 2.5 (m, 1H), 1.8 (br d, 1H), 1.4 (m, 2H), 0.85 (t, 3H).

(3S,4R,5R)-3-(Difluoromethyl)-4,5-dihydroxy-N-phenylpiperidine-1-carboxamide (9b; X=O; R⁵=phenyl)

Following General Procedure E and using phenyl isocyanate (0.14 g, 1.2 mmol) the title compound was obtained as a white solid (0.21 g, 62%). MH$^+$=287. $^1$H NMR (DMSO-d$_6$) 8.7 (s, 1H), 7.45 (d, 2H), 7.3 (t, 2H), 6.95 (t, 1H), 6.3 (t, 1H, J=53 Hz), 5.35 (d, 1H), 5.25 (d, 1H), 4.1 (t, 2H), 3.3 (m, 2H), 2.85 (t, 1H), 2.75 (t, 1H), 1.95 (br d, 1H).

(3S,4R,5R)-3-(Difluoromethyl)-4,5-dihydroxy-N-butylpiperidine-1-carboxamide (9c; X=O; R⁵=butyl)

Following General Procedure E and using butyl isocyanate (0.12 g, 1.2 mmol) the title compound was obtained as a white solid (0.24 g, 76%). MH$^+$=267. $^1$H NMR (DMSO-d$_6$) 6.6 (t, 1H), 6.2 (t, 1H, J=53 Hz), 5.25 (d, 1H), 5.1 (d, 1H), 4.05 (d, 1H), 3.9 (d, 1H), 3.35 (m, 2H), 3.05 (q, 2H), 2.65 (t, 1H), 2.45 (m, 1H), 1.8 (br d, 1H), 1.2-1.4 (2 m, 4H), 0.85 (t, 3H).

(3S,4R,5R)-3-(Difluoromethyl)-4,5-dihydroxy-N-butylpiperidine-1-carbthioamide (9d; X=S; R⁵=butyl)

Following General Procedure E and using butyl isothiocyanate (0.14 g, 1.2 mmol) the title compound was obtained as a colorless syrup (0.21 g, 63%). MH$^+$=283. $^1$H NMR (DMSO-d$_6$) 7.85 (t, 1H), 6.25 (t, 1H), 5.35 (2d, 2H), 4.8 (d, 1H), 4.45 (d, 1H), 3.45 (m, 2H), 3.25 (m, 1H), 3.05 (t, 1H), 2.8 (t, 1H), 1.85 (br d, 1H), 1.4 (m, 2H), 1.35 (m, 2H), 1.1 (m, 1H), 0.95 (t, 3H).

(3S,4R,5R)-3-(Difluoromethyl)-4,5-dihydroxy-N-phenylpiperidine-1-carbthioamide (9e; X=S; R⁵=phenyl)

Following General Procedure E and using phenyl isothiocyanate (0.16 g, 1.2 mmol) the title compound was obtained as a white solid (0.31 g, 86%). MH$^+$=303. $^1$H NMR (DMSO-d$_6$) 9.5 (s, 1H), 7.3 (m, 4H), 7.1 (t, 1H), 6.35 (t, 1H), 5.35 (2d, 2H), 4.85 (d, 1H), 4.55 (d, 1H), 3.45 (m, 2H), 3.2 (t, 1H), 3.0 (t, 1H), 2.05 (br d, 1H).

Compounds of the present invention can also be made by one skilled in the art using the following general schemes:

Scheme 3

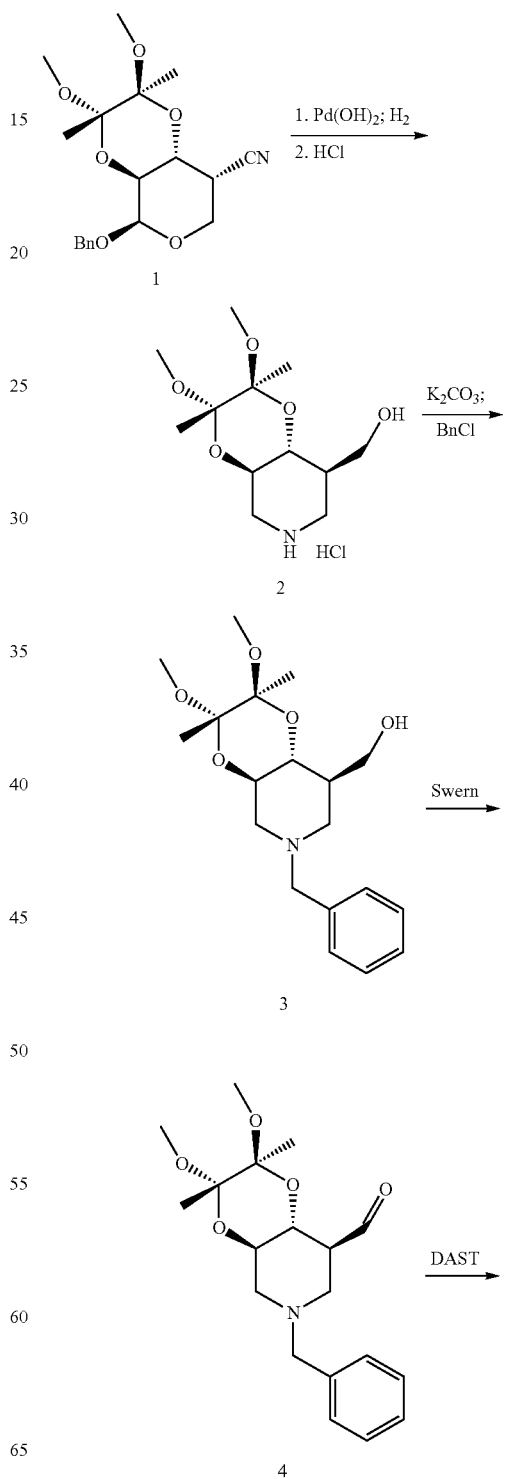

35
-continued
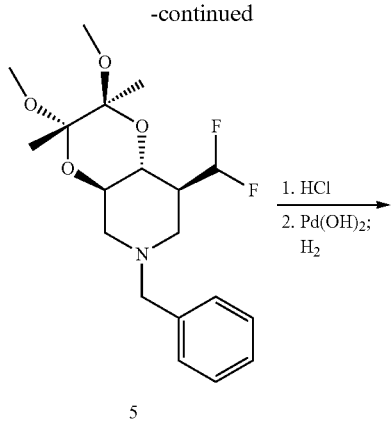
5
36
-continued
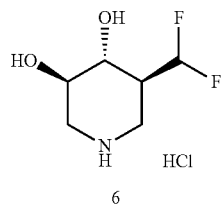 [SMILES: O[C@H]1[C@H](O)CNC[C@@H]1C(F)F ; Cl]
6
Scheme 4
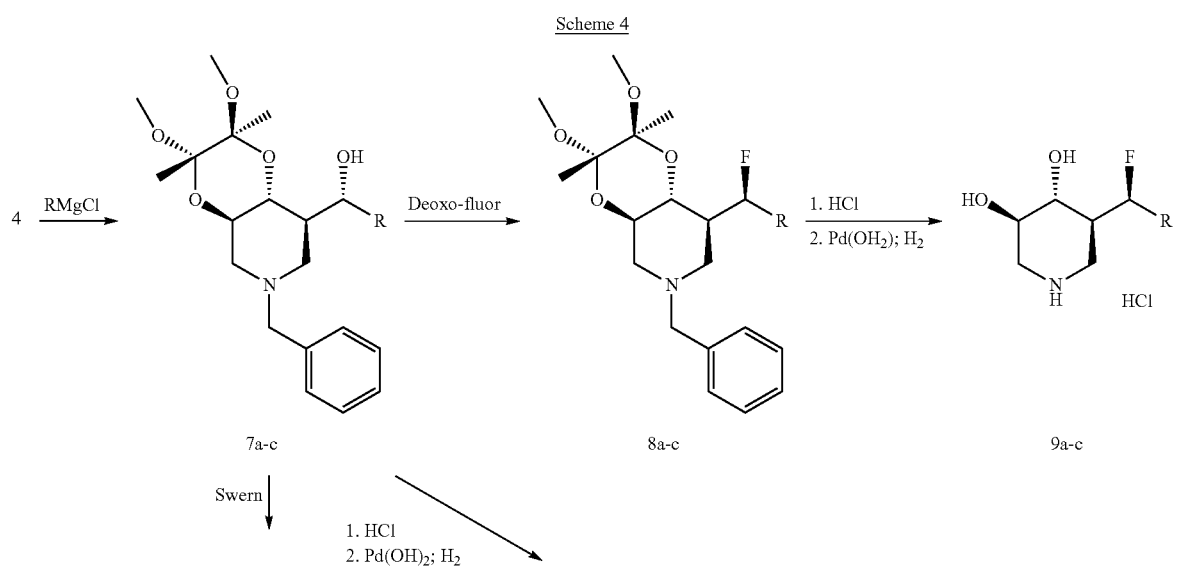
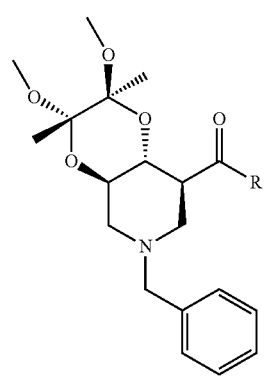
10a-c
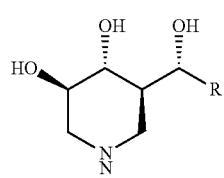
14a-c

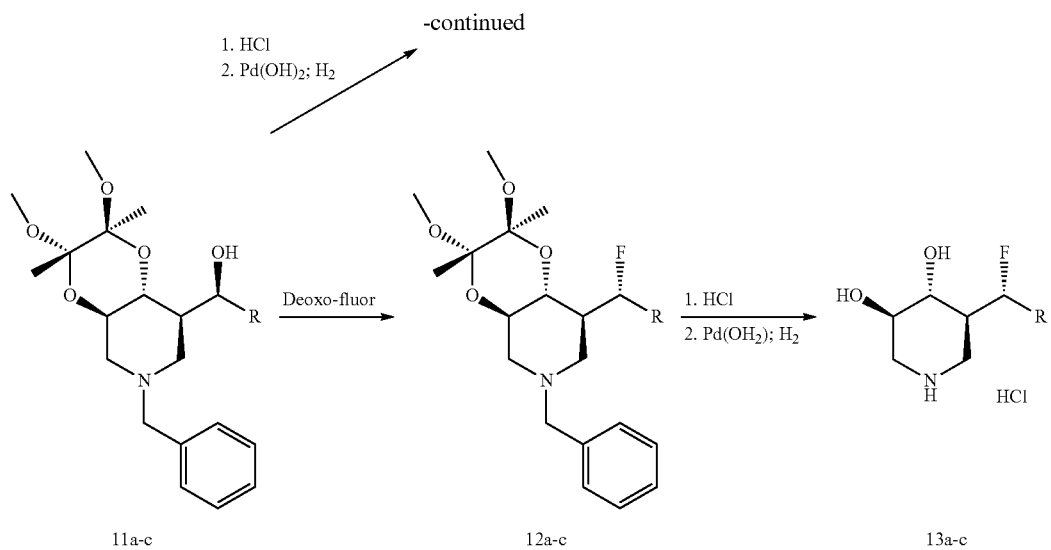
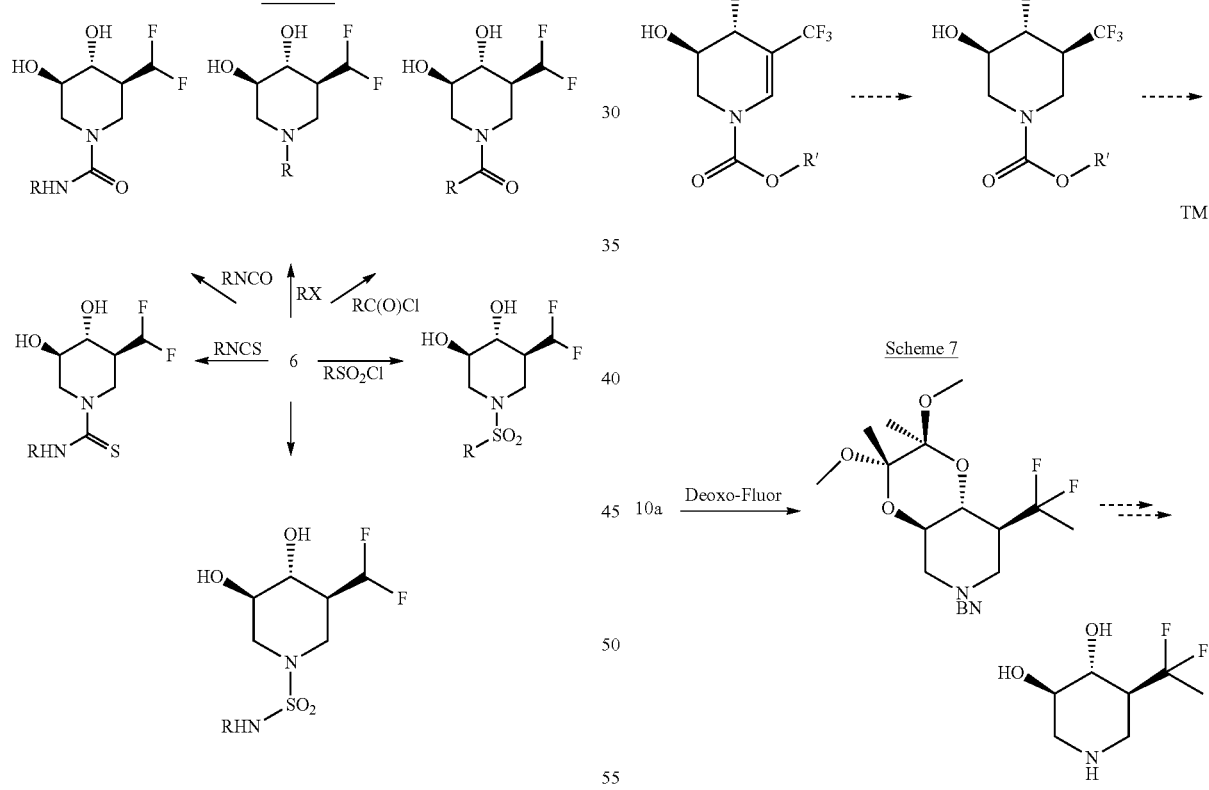
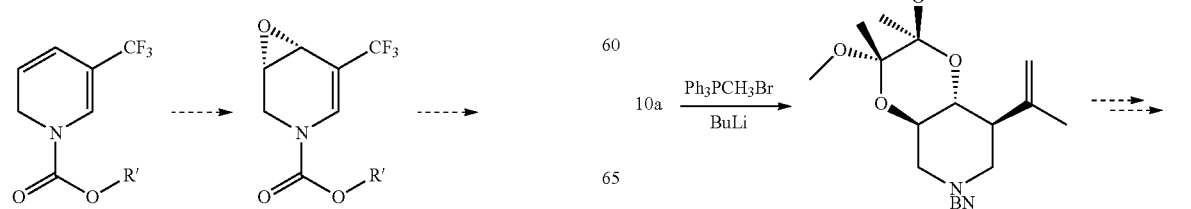

-continued

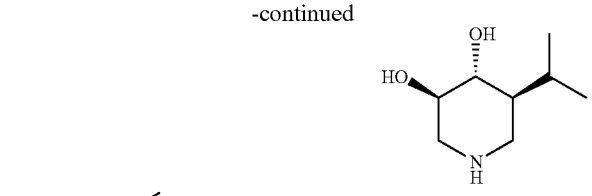

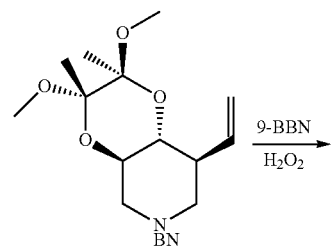

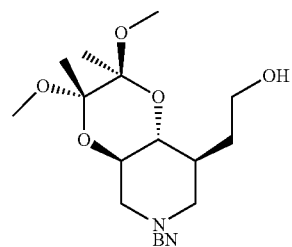

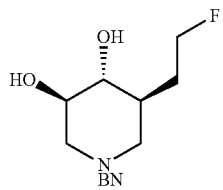

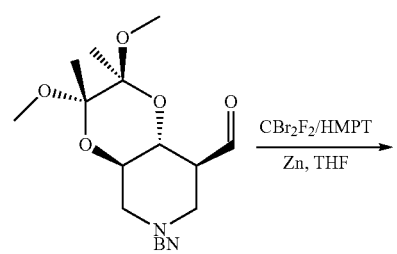

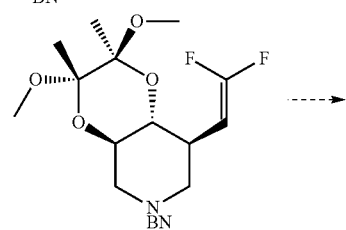

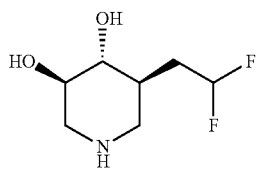

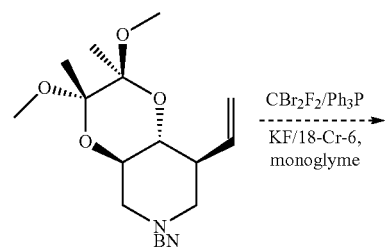

-continued

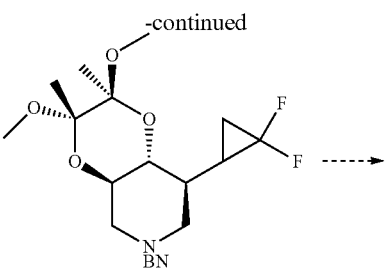

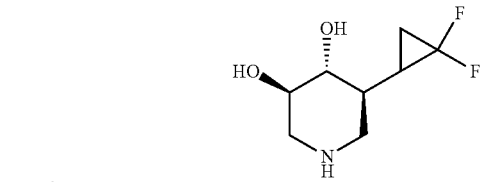

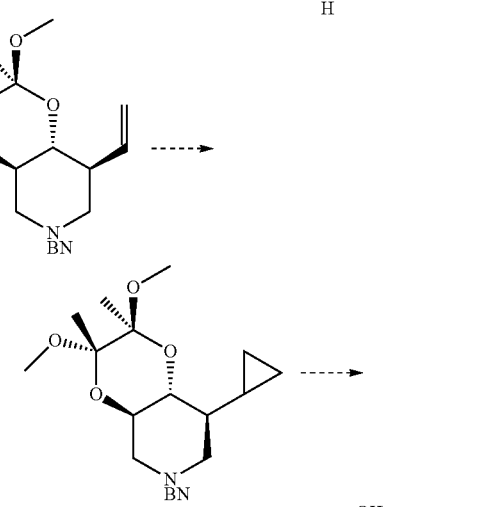

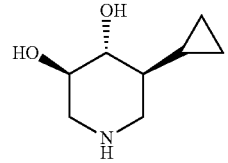

Salts, Solvates and Prodrugs

Compounds of the present invention include pharmaceutically acceptable salts, solvates and pro-drugs of the compounds disclosed herein. Pharmaceutically acceptable salts include salts derived from inorganic bases such as Li, Na, K, Ca, Mg, Fe, Cu, Zn, Mn; salts of organic bases such as N,N'-diacetylethylenediamine, glucamine, triethylamine, choline, hydroxide, dicyclohexylamine, metformin, benzylamine, trialkylamine, thiamine; chiral bases like alkylphenylamine, glycinol, phenyl glycinol, salts of natural amino acids such as glycine, alanine, valine, leucine, isoleucine, norleucine, tyrosine, cystine, cysteine, methionine, proline, hydroxy proline, histidine, ornithine, lysine, arginine, serine; non-natural amino acids such as D-isomers or substituted amino acids; guanidine, substituted guanidine wherein the substituents are selected from nitro, amino, alkyl, alkenyl, alkynyl, ammonium or substituted ammonium salts and aluminum salts. Salts may include acid addition salts where appropriate which are, hydrochlorides, sulphates, nitrates, phosphates, perchlorates, borates, hydrohalides, acetates, tartrates, maleates, citrates, succinates, palmoates, methanesulphonates, benzoates, salicylates, benzenesulfonates, ascorbates, glycerophosphates, ketoglutarates. In one embodiment, the pharmaceutically acceptable salt of the compounds disclosed herein is the hydrochloride salt.

"Solvate" denotes a physical association of a compound with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. "Hydrate" is a solvate wherein the solvent molecule is $H_2O$. Other non-limiting examples of suitable solvates include alcohols (e.g., ethanolates, methanolates, and the like).

Prodrugs are compounds which are converted in vivo to active forms (see, e.g., R. B. Silverman, 1992, "The Organic Chemistry of Drug Design and Drug Action", Academic Press, Chapter 8, incorporated herein by reference). Additionally, a discussion of prodrugs is provided in T. Higuchi and V. Stella, Pro-drugs as Novel Delivery Systems, Volume 14 of the A.C.S. Symposium Series, and in Bioreversible Carriers in Drug Design, Edward B. Roche, ed., American Pharmaceutical Association and Pergamon Press, 1987, both of which are incorporated herein by reference thereto. Prodrugs can be used to alter the biodistribution (e.g., to allow compounds which would not typically enter the reactive site of the protease) or the pharmacokinetics for a particular compound. For example, a carboxylic acid group, can be esterified, e.g., with a methyl group or an ethyl group to yield an ester. When the ester is administered to a subject, the ester is cleaved, enzymatically or non-enzymatically, reductively, oxidatively, or hydrolytically, to reveal the anionic group. An anionic group can be esterified with moieties (e.g., acyloxymethyl esters) which are cleaved to reveal an intermediate compound which subsequently decomposes to yield the active compound.

Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound with a suitable derivatizing agent. For example hydroxy groups can be converted into esters via treatment with a carboxilic acid in the presence of a catalyst. Examples of cleavable alcohol prodrug moieties include substituted and unsubstituted, branched or unbranched lower alkyl ester moieties, (e.g., ethyl esters), lower alkenyl esters, di-lower alkyl-amino lower-alkyl esters (e.g., dimethylaminoethyl ester), acylamino lower alkyl esters, acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides.

All stereoisomers (for example, geometric isomers, optical isomers and the like) of the compounds disclosed herein (including those of the salts, solvates and prodrugs of these compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of these compounds may, for example, be substantially free of other isomers, or may be admixed, for example, as racemates or with all other, or other selected, stereoisomers. The chiral centers of the aforementioned compounds can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the compounds of the present invention disclosed herein.

Formulations

The therapeutic agent(s) can be formulated to be suitable for any route of administration, including e.g., orally in the form of tablets or capsules or liquid, or in sterile aqueous solution for injection. When the therapeutic agent(s) is formulated for oral administration, tablets or capsules can be prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or another suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); or preservatives (e.g., methyl or propyl-p-hydroxybenzoates or sorbic acid). The liquid preparations may also contain buffer salts, flavoring, coloring or sweetening agents as appropriate. Preparations for oral administration may be suitably formulated to give controlled or sustained release of the therapeutic agent(s).

In certain embodiments of the present invention, the therapeutic agent(s) is administered in a dosage form that permits systemic uptake, such that the therapeutic agent(s) may cross the blood-brain barrier so as to exert effects on neuronal cells. For example, pharmaceutical formulations of the therapeutic agent(s) suitable for parenteral/injectable use generally include sterile aqueous solutions (where water soluble), or dispersions and sterile powders for the extemporaneous preparation of sterile injectable solutions or dispersion. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, polyethylene glycol, and the like), suitable mixtures thereof, or vegetable oils. The proper fluidity can be maintained, for example, by the use of a coating such as lecithin, by the maintenance of the required particle size in the case of dispersion and by the use of surfactants. Prevention of the action of microorganisms can be brought about by various antibacterial and antifungal agents, for example, parabens, chlorobutanol, phenol, benzyl alcohol, sorbic acid, and the like. In many cases, it will be reasonable to include isotonic agents, for example, sugars or sodium chloride. Prolonged absorption of the injectable compositions can be brought about by the use in the compositions of agents delaying absorption, for example, aluminum monosterate or gelatin.

Sterile injectable solutions are prepared by incorporating the therapeutic agent(s) in the required amount in the appropriate solvent with various of the other ingredients enumerated above, as required, followed by filter or terminal sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

The formulation can contain an excipient. Pharmaceutically acceptable excipients which may be included in the formulation are buffers such as citrate buffer, phosphate buffer, acetate buffer, and bicarbonate buffer, amino acids, urea, alcohols, ascorbic acid, phospholipids; proteins, such as serum albumin, collagen, and gelatin; salts such as EDTA or EGTA, and sodium chloride; liposomes; polyvinylpyrollidone; sugars, such as dextran, mannitol, sorbitol, and glycerol; propylene glycol and polyethylene glycol (e.g., PEG-4000, PEG-6000); glycerol; glycine or other amino acids; and lipids. Buffer systems for use with the formulations include citrate; acetate; bicarbonate; and phosphate buffers. Phosphate buffer is a preferred embodiment.

The formulation can also contain a non-ionic detergent. Preferred non-ionic detergents include Polysorbate 20, Polysorbate 80, Triton X-100, Triton X-114, Nonidet P-40, Octyl α-glucoside, Octyl β-glucoside, Brij 35, Pluronic, and Tween 20.

Routes of Administration

The therapeutic agent(s) may be administered orally or parenterally, including intravenously, subcutaneously, intraarterially, intraperitoneally, ophthalmically, intramuscularly, buccally, rectally, vaginally, intraorbitally, intracerebrally, intradermally, intracranially, intraspinally, intraventricularly, intrathecally, intracisternally, intracapsularly, intrapulmonarily, intranasally, transmucosally, transdermally, or via inhalation. In one preferred embodiment, the therapeutic agent(s) is administered orally.

Administration of therapeutic agent(s) may be by periodic injections of a bolus of the formulation, or may be administered by intravenous or intraperitoneal administration from a reservoir which is external (e.g., an i.v. bag) or internal (e.g., a bioerodable implant). See, e.g., U.S. Pat. Nos. 4,407,957 and 5,798,113, each incorporated herein by reference. Intrapulmonary delivery methods and apparatus are described, for example, in U.S. Pat. Nos. 5,654,007, 5,780,014, and 5,814,607, each incorporated herein by reference. Other useful parenteral delivery systems include ethylene-vinyl acetate copolymer particles, osmotic pumps, implantable infusion systems, pump delivery, encapsulated cell delivery, liposomal delivery, needle-delivered injection, needle-less injection, nebulizer, aerosolizer, electroporation, and transdermal patch. Needle-less injector devices are described in U.S. Pat. Nos. 5,879,327; 5,520,639; 5,846,233 and 5,704,911, the specifications of which are herein incorporated by reference. Any of the formulations described above can be administered using these methods.

Subcutaneous injections have the advantages allowing self-administration, while also resulting in a prolonged plasma half-life as compared to intravenous administration. Furthermore, a variety of devices designed for patient convenience, such as refillable injection pens and needle-less injection devices, may be used with the formulations of the present invention as discussed herein.

Dosage

A suitable pharmaceutical preparation is in a unit dosage form. In such form, the preparation is subdivided into suitably sized unit doses containing appropriate quantities of the active component, e.g., an effective amount to achieve the desired purpose. In certain embodiments, the therapeutic agent(s) is administered in one or more daily doses (e.g., once-a-day, twice-a-day, thrice-a-day). In certain embodiments, the therapeutic agent(s) is administered in intermittently.

Exemplary dosing regimens are described in International patent application PCT/US08/61764 published as WO 2008/134628 on Jun. 11, 2008 and U.S. provisional patent application 61/108,192, filed on Oct. 24, 2008, both of which are incorporated by reference herein in their entirety. In one embodiment, the therapeutic agent(s) is administered in an intermittent dosing regimen that includes an initial "loading dose" given daily, followed by a period of non-daily interval dosing.

The amount of effective therapeutic agent(s) for preventing or treating the referenced disorder can be determined on a case-by-case basis by those skilled in the art. The amount and frequency of administration of the therapeutic agent(s) will be regulated according to the judgment of the attending clinician (physician) considering such factors as age, condition and size of the patient as well as risk for developing disorder or severity of the symptoms of the referenced disorder being treated.

Combination Drug Therapy

The therapeutic agent(s) of the present invention can be administered in combination with at least one other therapeutic agent. Administration of the therapeutic agent(s) of the present invention with at least one other therapeutic agent is understood to encompass administration that is sequential or concurrent. In one embodiment, the therapeutic agents are administered in separate dosage forms. In another embodiment, two or more therapeutic agents are administered concurrently in the same dosage form.

In certain embodiments, the therapeutic agent(s) of the present invention are administered in combination with at least one other therapeutic agent which is an anti-dyskinesia Agent (e.g., Carbidopa, Levodopa), an anti-infective agent (e.g., Miglustat), an antineoplastic agent (e.g., Busulfan, Cyclophosphamide), a gastrointestinal agent (e.g., Methylprednisolone), a micronutrient (e.g., Calcitriol, Cholecalciferol, Ergocalciferols, Vitamin D), a vasoconstrictor agent (e.g., Calcitriol).

In certain embodiments, the therapeutic agent(s) of the present invention are administered in combination with allopregnanolone, a low-cholesterol diet, or cholesterol-lowering agents such as statins (e.g., Lipitor®); fibrates such as fenofibrate (Lipidil®); niacin; and/or binding resins such as cholestyramine (Questran®).

In one embodiment, the therapeutic agent(s) of the present invention is administered in combination with gene therapy. Gene therapy is contemplated both with replacement genes such as glucocerebrosidase or with inhibitory RNA (siRNA) for the SNCA gene. Gene therapy is described in more detail in U.S. Pat. No. 7,446,098, filed on Feb. 17, 2004.

In one embodiment, the therapeutic agent(s) of the present invention is administered in combination with at least one other therapeutic agent which is an anti-inflammatory agent (e.g., ibuprofen or other NSAID).

In one embodiment, the therapeutic agent(s) of the present invention is administered in combination with a substrate inhibitor for glucocerebrosidase, such as N-butyl-deoxynojirimycin (Zavesca®; miglustat available from Actelion Pharmaceuticals, US, Inc., South San Francisco, Calif., US).

Combinations of the therapeutic agent(s) of the present invention with at least one other therapeutic agent which is a therapeutic agent for one or more other lysosomal enzymes are also contemplated. Following is a non-limiting list of therapeutic agents for lysosomal enzymes.

TABLE 1

| LYSOSOMAL ENZYME | THERAPEUTIC AGENT |
|---|---|
| α-Glucosidase<br>GenBank Accession No. Y00839 | 1-deoxynojirimycin (DNJ)<br>α-homonojirimycin<br>castanospermine |
| Acid β-Glucosidase (β-<br>glucocerebrosidase)<br>GenBank Accession No. J03059 | isofagomine<br>C-benzyl isofagomine and derivatives<br>N-alkyl (C9-12)-DNJ<br>Glucoimidazole (and derivatives)<br>C-alkyl-IFG (and derivatives)<br>N-alkyl-β-valeinamines<br>Fluphenozine<br>calystegines $A_3$, $B_1$, $B_2$ and $C_1$ |
| α-Galactosidase A<br>GenBank Accession No. NM000169 | 1-deoxygalactonojirimycin (DGJ)<br>α-allo-homonojirimycin<br>α-galacto-homonojirimycin<br>β-1-C-butyl-deoxynojirimycin<br>calystegines $A_2$ and $B_2$<br>N-methyl calystegines $A_2$ and $B_2$ |
| Acid β-Galactosidase<br>GenBank Accession No. M34423 | 4-epi-isofagomine<br>1-deoxygalactonojirimyicn |
| Galactocerebrosidase (Acid β-<br>Galactosidase)<br>GenBank Accession No. D25283 | 4-epi-isofagomine<br>1-deoxygalactonojirimycin |
| Acid α-Mannosidase<br>GenBank Accession No. U68567 | 1-deoxymannojirimycin<br>Swainsonine<br>Mannostatin A |
| Acid β-Mannosidase<br>GenBank Accession No. U60337 | 2-hydroxy-isofagomine |
| Acid α-L-fucosidase<br>GenBank Accession No. NM_000147 | 1-deoxyfuconojirimycin<br>β-homofuconojirimycin<br>2,5-imino-1,2,5-trideoxy-L-glucitol<br>2,5-deoxy-2,5-imino-D-fucitol<br>2,5-imino-1,2,5-trideoxy-D-altritol |
| α-N-Acetylglucosaminidase<br>GenBank Accession No. U40846 | 1,2-dideoxy-2-N-acetamido-nojirimycin |
| α-N-Acetylgalactosaminidase<br>GenBank Accession No. M62783 | 1,2-dideoxy-2-N-acetamido-<br>galactonojirimycin |
| β-Hexosaminidase A<br>GenBank Accession No. NM_000520 | 2-N-acetylamino-isofagomine<br>1,2-dideoxy-2-acetamido-nojirimycin<br>Nagstatin |
| β-Hexosaminidase B<br>GenBank Accession No. NM_000521 | 2-N-acetamido-isofagomine<br>1,2-dideoxy-2-acetamido-nojirimycin<br>Nagstatin |
| α-L-Iduronidase<br>GenBank Accession No. NM_000203 | 1-deoxyiduronojirimycin<br>2-carboxy-3,4,5-trideoxypiperidine |
| β-Glucuronidase<br>GenBank Accession No. NM_000181 | 6-carboxy-isofagomine<br>2-carboxy-3,4,5-trideoxypiperidine |
| Sialidase<br>GenBank Accession No. U84246 | 2,6-dideoxy-2,6, imino-sialic acid<br>Siastatin B |
| Iduronate sulfatase<br>GenBank Accession No. AF_011889 | 2,5-anhydromannitol-6-sulphate |
| Acid sphingomyelinase<br>GenBank Accession No. M59916 | desipramine, phosphatidylinositol-4,5-<br>diphosphate |

In certain embodiments, the therapeutic agent(s) of the present invention are administered in combination with at least one therapeutic agent which is an anti-dyskinesia Agent (e.g., Carbidopa, Levodopa), an anti-infective agent (e.g., Cyclosporine, Miglustat, Pyrimethamine), an antineoplastic agent (e.g., Alemtuzumab, Azathioprine, Busulfan, Clofarabine, Cyclophosphamide, Melphalan, Methotrexate, Rituximab), an antirheumatic agent (e.g., Rituximab) a gastrointestinal agent (e.g., Methylprednisolone), a micronutrient (e.g., Calcitriol, Cholecalciferol, Ergocalciferols, Folic Acid, Vitamin D), a reproductive control agent (e.g., Methotrexate), a respiratory system agent (e.g., Tetrahydrozoline), vasoconstrictor agent (e.g., Calcitriol, Tetrahydrozoline).

In certain embodiments, the therapeutic agent(s) of the present invention are administered in combination with at least one therapeutic agent which is a therapeutic agent for β-hexosaminidase A and/or a therapeutic agent for acid β-galactosidase. In certain embodiments, the therapeutic agent(s) of the present invention are administered in combination with at least one therapeutic agent which is an anti-infective agent (e.g., Miglustat), an antineoplastic agent (e.g., Alemtuzumab, Busulfan, Cyclophosphamide), a gastrointestinal agent (e.g., Methylprednisolone).

The therapeutic agent(s) of the present invention can be administered in combination with at least one other therapeutic agent which includes but is not limited to, RNAi, dopamine replacement (e.g., levadopa (L-DOPA)), dopamine replacement stabilizer (e.g., carbidopa, and entacapone), anticholinergic (e.g., trihexyphenidyl, benzotropine mesylate (Cogentin®), trihexyphenidyl HCL (Artane®), and procyclidine), catechol-O-methyltransferase (COMT) inhibitor (e.g., entacapone (Comtan®) and tolcapone (Tasmar®)), dopamine receptor agonist (e.g., bromocriptine (Parlodel®), pramipexole (Mirapex®), ropinirole (Requip®)), pergolide (Permax), and APOKYN™ injection (apomorphine hydrochloride), monoamine oxidase (MAO) inhibitor (i.e., MAO-A and/or MAO-B inhibitors, e.g., selegiline (Deprenyl, Eldepryl®, Carbex®), selegiline HCl orally disintegrating tablet (Zelapar®), and rasagiline (Azilect®)), peripheral decarboxylase inhibitor, amantadine (Symmetrel®), and rivastigmine tartrate (Exelon®).

Also contemplated are combinations of the therapeutic agent(s) of the present invention with more than one other therapeutic agent. Exemplary combinations of other therapeutic agents include, but are not limited to, carbidopa/levodopa (Sinemet® or Parcopa®), carbidopa, levodopa and entacapone (Stalevo®), levodopa with a dopamine receptor agonist such as bromocriptine (Parlodel®), pramipexole (Mirapex®), ropinirole (Requip®)), pergolide (Permax), or APOKYN™ injection (apomorphine hydrochloride).

In one embodiment, the therapeutic agent(s) of the present invention is administered in combination with vaccine therapy, such as a vaccine comprising alpha-synuclein and an adjuvant (Pilcher et al., *Lancet Neurol.* 2005; 4(8):458-9).

In one embodiment, the therapeutic agent(s) of the present invention is administered in combination with at least one other therapeutic agent that may be protective such as dextromethorphan (Li et al., *FASEB J.* 2005; April; 19(6):489-96); genistein (Wang et al., *Neuroreport.* 2005; February 28; 16(3):267-70), or minocycline (Blum et al., *Neurobiol Dis.* 2004; December; 17(3):359-66).

In one embodiment, the therapeutic agent(s) of the present invention is administered in combination with at least one other therapeutic agent which is therapeutic agent for alpha-synuclein (e.g., Hsp70).

Patients having Parkinson's disease experience tremor, rigidity, bradykinesia, and postural imbalance. Patients having Lewy Body Dementia experience strong psychotic symptoms (visual hallucinations) in addition to mental decline such as memory loss and an inability to carry out simple tasks. Observable improvements in symptoms, or a delay of onset of certain symptoms in patients at risk of developing a disorder, or a delay in progression of the disorder will be evidence of a favorable response to the therapies provided herein.

In addition, measurable surrogate markers also may be useful for evaluating response to therapy. For instance, some investigators have reported detecting higher levels of alpha-synuclein or oligomeric forms of alpha-synuclein have been detected in the plasma of patients with Parkinson's disease (Lee et al., *J Neural Transm.* 2006; 113(10):1435-9; El-Agnaf et al., *FASEB J.* 2006; 20(3):419-25), while some have reported decreased plasma alpha-synuclein in Parkinson's patients compared with normal controls (Li et al., Exp Neurol. 2007; 204(2):583-8).

In certain embodiments, the therapeutic agent(s) of the present invention is administered in combination with at least one other therapeutic agent which is an alcohol deterrent (e.g., Acamprosate), a narcotic analgesic (e.g., Remifentanil), an anti-dyskinesia agent (e.g, Amantadine, Apomorphine, Benserazide, Bromocriptine, Cabergoline, Carbidopa, Dexetimide, Droxidopa, Entacapone, Levodopa, Lisuride, Memantine, Piribedil, Pramipexol, Ropinirole, Selegiline, Sinemet), an anti-infective agent (e.g, Amantadine, Amoxicillin, Clarithromycin, Ethanol, Interferons, Minocycline, PS-K), an anti-obesity agent (e.g., Phenylpropanolamine, Topiramate), an anticonvulsant (e.g., Etiracetam, Topiramate), an antiemetic (e.g., Trimethobenzamide), an antihypertensive agent (e.g., Trandolapril), an antineoplastic agent (e.g., Cabergoline, PS-K), central nervous system depressant (e.g., Aripiprazole, Benzocaine, Clozapine, Cocaine, Dexmedetomidine, Diphenhydramine, Isoflurane, Lithium, Lithium Carbonate, Methylperon, Morphine, Propofol, Quetiapine, Raclopride, Remifentanil, Sodium Oxybate), a central nervous system stimulant (e.g., Caffeine citrate, Modafinil, Nicotine polacrilex), a coagulant (e.g., Arginine Vasopressin, Deamino Arginine Vasopressin, Vasopressins), a dermatologic agent (e.g., Loratadine, Promethazine), a gastrointestinal agent (e.g., Diphenhydramine, Domperidone, Omeprazole, Trimethobenzamide), a hypnotic and/or sedative (e.g., Remifentanil), a micronutrient (e.g., Alpha-Tocopherol, Coenzyme Q10, Ergocalciferols, Hydroxocobalamin, Iron, Tocopherol acetate, Tocopherols, Vitamin B 12, Vitamin D, Vitamin E), a neuroprotective agent (e.g., Eliprodil, Modafinil, Rasagiline, Rivastigmine, Topiramate), a nootropic agent (e.g., Donepezil, Etiracetam), a psychotropic drug (e.g., Aripiprazole, Citalopram, Clozapine, Duloxetine, Lithium, Lithium Carbonate, Methylperon, Nortriptyline, Paroxetine, Quetiapine, Raclopride, Venlafaxine), a respiratory system agent (e.g., Dextromethorphan, Guaifenesin, Ipratropium, Naphazoline, Oxymetazoline, Phenylephrine, Phenylpropanolamine), a vasoconstrictor agent (e.g., Naphazoline, Oxymetazoline, Phenylephrine, Phenylpropanolamine).

In one preferred embodiment, the aforementioned other therapeutic agents are administered when the disorder is Parkinson's disease.

In certain embodiments, the therapeutic agent(s) of the present invention is administered in combination with at least one other therapeutic agent which is a nicotinic alpha-7 agonist (e.g., MEM 3454 or MEM 63908 both of which are available from Memory Pharmaceuticals). In certain embodiments, the therapeutic agent(s) of the present invention is administered in combination with at least one other therapeutic agent which is R3487 and/or R4996 (both of which are available from Roche). Also contemplated are combinations of the therapeutic agent(s) of the present invention with more than one other therapeutic agents. Exemplary combinations of other therapeutic agents include, but are not limited to, R3487/MEM 3454 and R4996/MEM 63908.

In certain embodiments, the therapeutic agent(s) of the present invention is administered in combination with at least one cholinesterase inhibitor (e.g., donepezil (brand name Aricept), galantamine (brand name Razadyne), and rivastigmine (branded as Exelon and Exelon Patch).

In certain embodiments, the therapeutic agent(s) of the present invention is administered in combination with at least one noncompetitive NMDA receptor antagonist (e.g., memantine (brand names Akatinol, Axura, Ebixa/Abixa, Memox and Namenda)).

In certain embodiments, the therapeutic agent(s) of the present invention is administered in combination with at least one other therapeutic agent which is a non-narcotic analgesic (e.g., Celecoxib, Resveratrol, Rofecoxib, TNFR-Fc fusion protein), an anti-dyskinesia agent (e.g., Dexetimide, Gabapentin, Levodopa, Memantine), an anti-infective agent (e.g., Acetylcysteine, Acyclovir, Benzoates, Deoxyglucose, Doxycycline, Interferon Alfa-2a, Interferon-alpha, Interferons, Moxifloxacin, PS-K, Quinacrine, Rifampin, Salicylic Acid, Valacyclovir), an anti-Inflammatory agent (e.g., Aspirin, Celecoxib, Curcumin, Ibuprofen, Indomethacin, Naproxen, Resveratrol, Rofecoxib, TNFR-Fc fusion protein), an anti-obesity agent (e.g., Phenylpropanolamine), an anticonvulsant agent (e.g., Gabapentin, Homotaurine, Lamotrigine), an antiemetic (e.g., Olanzapine), an antihypertensive agent (e.g., Trandolapril), an antilipemic agent (e.g., Atorvastatin, Choline, Clofibric Acid, Pravastatin, Simvastatin), an antineoplastic agent (e.g., Bryostatin 1, Carmustine, Cyclophosphamide, Interferon Alfa-2a, Leuprolide, Medroxyprogesterone 17-Acetate, Methyltestosterone, PK 11195, Prednisone, PS-K, Resveratrol, 2,3-dihydro-1H-imidazo[1,2-b]pyrazole), an antirheumatic agent (e.g., Aspirin, Celecoxib, Curcumin, Ibuprofen, Indomethacin, Naproxen, Resveratrol, Rofecoxib, TNFR-Fc fusion protein), a central nervous system depressant (e.g., Aripiprazole, Benzocaine, Cocaine, Gabapentin, Haloperidol, Haloperidol decanoate, Lithium, Lithium Carbonate, Lorazepam, Midazolam, Olanzapine, Perphenazine, Propofol, Quetiapine, Risperidone, Sodium Oxybate, Trazodone, Valproic Acid, Zolpidem), a central nervous system stimulant (e.g., Caffeine citrate, Modafinil, Nicotine polacrilex), a channel blocker (e.g., Gabapentin, Lamotrigine), a coagulant (e.g., Antiplasmin, Vitamin K), a dermatologic agent (e.g., Mineral Oil, Salicylic Acid), a gastrointestinal agent (e.g., Choline, Haloperidol, Lorazepam, Olanzapine, Omeprazole, TNFR-Fc fusion protein), a hypnotic and/or sedative agent (e.g., Zolpidem), a hypoglycemic agent (e.g., Insulin, Asp(B28)-, Rosiglitazone), a micronutrient (e.g., Alpha-Tocopherol, Ascorbic Acid, Coenzyme Q10, Copper, Folic Acid, Hydroxocobalamin, Inositol, Iron, Niacin, Niacinamide, Nicotinic Acids, Pyridoxine, Selenium, Thioctic Acid, Tocopherol acetate, Tocopherols, Vitamin B 12, Vitamin B 6, Vitamin E, Vitamin K), a neuroprotective agent (e.g., Huperzine A, Modafinil, Nefiracetam, Rasagiline, Rivastigmine, (3-aminopropyl)(n-butyl)phosphinic acid), a nootropic agent (e.g., Donepezil, Nefiracetam), a platelet aggregation inhibitor (e.g., Resveratrol), a psychotropic drug (e.g., Aripiprazole, Bupropion, Citalopram, Duloxetine, Gabapentin, Haloperidol, Haloperidol decanoate, Lithium, Lithium Carbonate, Lorazepam, Midazolam, Nefiracetam, Olanzapine, Paroxetine, Perphenazine, Quetiapine, Risperidone, Sertraline, Trazodone, Tryptophan, Valproic Acid, Venlafaxine), a reproductive control agent (e.g., Estradiol 17 beta-cypionate, Estradiol 3-benzoate, Estradiol valerate, Indomethacin, Leuprolide, Medroxyprogesterone, Medroxyprogesterone 17-Acetate, Mifepristone), a respiratory system agent (e.g., Acetylcysteine, Dextromethorphan, Guaifenesin, Naphazoline, Oxymetazoline, Phenylephrine, Phenylpropanolamine), or a vasoconstrictor agent (e.g., Naphazoline, Oxymetazoline, Phenylephrine, Phenylpropanolamine).

In one preferred embodiment, the aforementioned other therapeutic agents are administered when the disorder is Alzheimer's disease.

EXAMPLES

The present invention is further described by means of the examples, presented below. The use of such examples is illustrative only and in no way limits the scope and meaning of the invention or of any exemplified term. Likewise, the invention is not limited to any particular preferred embodiments described herein. Indeed, many modifications and variations of the invention will be apparent to those skilled in the art upon reading this specification. The invention is therefore to be limited only by the terms of the appended claims along with the full scope of equivalents to which the claims are entitled.

Example 1

Determination of Inhibition Constants

The binding affinity (defined here by $K_i$ binding constant) of GCase for novel compounds of the present invention were empirically determined using enzyme inhibition assays. In brief, the enzyme inhibition assays used monitored the ability of a test compound to bind and prevent the hydrolysis of a fluorogenic substrate in a concentration-dependent manner. Specifically, the enzyme activity of recombinant human GCase (rhGCase; Cerezyme®, Genzyme Corp.) was measured using the 4-methylumbelliferyl-β-D-glucopyranoside (4-MU-β-D-Glc) fluorogenic substrate in the absence or in the presence of varying amounts of each test compound. The resultant data were analyzed by comparing all test samples to the no inhibition control sample (no compound; corresponding to 100% enzyme activity) to determine the residual enzyme activity in the presence of test compound. The normalized residual activity data were subsequently graphed (on y-axis) relative to the concentration of test compound (on x-axis) to extrapolate the test compound concentration which leads to 50% inhibition of enzyme activity (defined as $IC_{50}$). The $IC_{50}$ value for each test compound was then inserted into the Cheng-Prusoff equation (detailed below) to derive the absolute inhibition constant $K_i$ that accurately reflects the binding affinity of GCase for the test compound. The enzyme inhibition assays were performed at both pH 7.0 (endoplasmic reticulum pH) and at pH 5.2 (lysosomal pH) to gain insight into the binding affinity (i.e., potency) of compounds for GCase in the endoplasmic reticulum and lysososome.

In Vitro Assay

Various concentrations of test compounds were prepared in buffer "M" consisting of 50 mM sodium phosphate buffer with 0.25% sodium taurocholate at pH 7.0 and pH 5.2. Enzyme (Cerezyme®, a recombinant form of the human enzyme β-glucocerebrosidase) was also diluted in the same buffer "M" at pH 7.0 and pH 5.2. The substrate solution consisted of 3 mM 4-methylumbelliferone β-D-glucopyranoside in buffer "M" with 0.15% Triton X-100 at both pH's. Five microliters of diluted enzyme was added to 15 µl of the various inhibitor concentrations or buffer "M" alone and incubated at 37° C. for 1 hour with 50 µl of the substrate preparation to assess β-glucosidase activity at pH 7.0 and pH 5.2. Reactions were stopped by addition of an equal volume of 0.4 M glycine, pH 10.6. Fluorescence was measured on a plate reader for 1 sec/well using 355 nm excitation and 460 nm emission. Incubations without added enzyme or without added inhibitors were used to define no enzyme activity and maximum activity, respectively, and normalize % inhibition for a given assay. The results of such in vitro inhibition assays for reference compound IFG-tartrate and several test compounds are summarized below in Table 2A

TABLE 2A

| | | In vitro Determination of Inhibition Constants | | | |
|---|---|---|---|---|---|
| Cmpd # | Compound Name | $IC_{50}$ (µM) pH 5.2 | $K_i$ (µM) pH 5.2 | $IC_{50}$ (µM) pH 7.0 | $K_i$ (µM) pH 7.0 |
| 6 | (3R,4R,5S)-5-(difluoromethyl)-piperidine-3,4-diol | 0.0259 ± 0.0014 | 0.0136 ± 0.0008 | 0.0058 ± 0.00023 | 0.00306 ± 0.00012 |
| 13 | (3R,4R,5S)-5-(1-fluoroethyl)-piperidine-3,4-diol* | 0.0946 ± 0.0028 | 0.0498 ± 0.0015 | 0.0171 ± 0.0008 | 0.009 ± 0.0004 |

TABLE 2A-continued

In vitro Determination of Inhibition Constants

| Cmpd # | Compound Name | IC$_{50}$ (μM) pH 5.2 | K$_i$ (μM) pH 5.2 | IC$_{50}$ (μM) pH 7.0 | K$_i$ (μM) pH 7.0 |
|---|---|---|---|---|---|
| 9 | (3R,4R,5R)-5-(1-hydroxyethyl)-piperidine-3,4-diol* | 0.107 ± 0.0041 | 0.044 ± 0.0017 | 0.020 ± 0.0008 | 0.010 ± 0.0004 |
| 10 | (3R,4R,5R)-5-(1-hydroxyethyl)-piperidine-3,4-diol* | 0.343 ± 0.021 | 0.142 ± 0.0088 | 0.066 ± 0.0041 | 0.035 ± 0.0021 |
| 14 | (3R,4R,5S)-5-(1-fluoroethyl)-piperidine-3,4-diol* | 0.038 ± 0.0016 | 0.016 ± 0.0007 | 0.007 ± 0.0003 | 0.004 ± 0.0001 |
| none | (3R,4R,5S)-5-((R)-1-fluoropropyl)-piperidine-3,4-diol hydrochloride | 0.291 ± 0.006 | 0.121 ± 0.0026 | 0.060 ± 0.0029 | 0.031 ± 0.0015 |
| none | (3R,4R,5S)-5-benzyl-piperidine-3,4-diol | 0.659 ± 0.028 | 0.273 ± 0.012 | 0.127 ± 0.01 | 0.067 ± 0.005 |
| none | (3R,4R,5R)-5-((S)-hydroxy(phenyl)methyl)-piperidine-3,4-diol | 3.29 ± 0.25 | 1.36 ± 0.10 | 0.017 ± 0.0035 | 0.0089 ± 0.0018 |
| none | (3R,4R,5S)-5-(2-hydroxypropan-2-yl)piperidine-3,4-diol | 0.234 ± 0.0037 | 0.097 ± 0.0015 | 0.029 ± 0.0013 | 0.015 ± 0.0007 |
| none | IFG-tartrate | 0.049 ± 0.0029 | 0.026 ± 0.0015 | 0.0074 ± 0.00007 | 0.0039 ± 0.000037 |

Notes:
*Stereoisomer A and/or B

In Situ Assay

The effect of the novel compounds of the present invention on lysosomal GCase activity was assayed in situ using fibroblasts established from a normal subject. Cells seeded in 48-well plates were incubated with the indicated concentrations of compound for 16-24 hours. For the dose-response assays, cells were incubated with the in situ substrate 5-(pentafluorobenzoylamino)fluorescein di-β-D-glucopyranoside (PFBFDβGlu) for 1 hour and subsequently lysed to determine the extent of substrate hydrolysis in the presence of compound. The assay employed a range of 12 concentrations encompassing 5 orders of magnitude, centered on the IC50. Specifically, the following concentration ranges were employed: (3R,4R,5S)-5-(difluoromethyl)piperidine-3,4-diol, (3R,4R,5S)-5-(1-fluoroethyl)piperidine-3,4-diol, (3R,4R,5R)-5-(1-hydroxyethyl)-piperidine-3,4-diol, (3R,4R,5S)-5-((R)-1-fluoropropyl)piperidine-3,4-diol hydrochloride, and (3R,4R,5S)-5-benzylpiperidine-3,4-diol: $1.0 \times 10^{-3}$ to $3.0 \times 10^{-9}$ M; (3R,4R,5R)-5-(1-hydroxyethyl)-piperidine-3,4-diol: $1.0 \times 10^{-4}$ to $3.0 \times 10^{-10}$ M; and (3R,4R,5S)-5-(1-fluoroethyl)piperidine-3,4-diol: $1.0 \times 10^{-3}$ to $3.0 \times 10^{-11}$ M; wherein compound was serially diluted 1:3 from the highest concentration in the ranges specified. Inhibition was determined as the ratio of activity in the presence of compound to that in the absence of compound. For the washout assays, cells were treated with compound for 16-24 hours at a concentration equal to the IC90. Cells were washed extensively and incubated in drug-free medium to allow net compound efflux from cells. Cells were then tested for lysosomal GCase activity at 2 hour intervals over a total period of 8 hours following compound removal. The increase in activity over time was fitted with a single exponential function to determine the compound's washout time. The results of these in situ inhibition assays for reference compound IFG-tartrate and several test compounds are summarized below in Table 2B.

TABLE 2B

In situ Determination of Inhibition Constants

| Cmpd # | Compound Name | In situ IC$_{50}$ (μM) | in situ washout (hr) | EC$_{50}$ (μM) | E$_{max}$ (%) |
|---|---|---|---|---|---|
| 6 | (3R,4R,5S)-5-(difluoromethyl)-piperidine-3,4-diol | 0.408 ± 0.046 | 2.1 ± 0.30 | 0.018 ± 0.008 | 105.6 ± 8.7 |
| 13 | (3R,4R,5S)-5-(1-fluoroethyl)-piperidine-3,4-diol* | 0.650 ± 0.172 | 2.7 ± 0.12 | 0.044 ± 0.005 | 92.8 ± 6.6 |
| 9 | (3R,4R,5R)-5-(1-hydroxyethyl)-piperidine-3,4-diol* | 0.518 ± 0.022 | 10.5 ± 1.75 | 0.49 ± 0.06 | 83.7 ± 2.9 |
| 10 | (3R,4R,5R)-5-(1-hydroxyethyl)-piperidine-3,4-diol* | 0.798 ± 0.043 | 12 ± 1.65 | 1.06 ± 0.12 | 99.3 ± 4.9 |
| 14 | (3R,4R,5S)-5-(1-fluoroethyl)-piperidine-3,4-diol* | 0.061 ± 0.019 | 3.7 ± 0.63 | 0.026 ± 0.003 | 89.7 ± 3.5 |
| none | (3R,4R,5S)-5-((R)-1-fluoropropyl)-piperidine-3,4-diol hydrochloride | 0.972 ± 0.201 | ND | 0.086 ± 0.002 | 84.0 ± 4.1 |

TABLE 2B-continued

In situ Determination of Inhibition Constants

| Cmpd # | Compound Name | In situ IC$_{50}$ (µM) | in situ washout (hr) | EC$_{50}$ (µM) | E$_{max}$ (%) |
|---|---|---|---|---|---|
| none | (3R,4R,5S)-5-benzyl-piperidine-3,4-diol | 1.299 ± 0.323 | 1.2 ± 0.13 | 0.18 ± 0.01 | 98.0 ± 4.5 |
| none | (3R,4R,5R)-5-((S)-hydroxy(phenyl)methyl)-piperidine-3,4-diol | ND | ND | 4.99 ± 0.86 | 72.1 ± 3.5 |
| none | (3R,4R,5S)-5-(2-hydroxypropan-2-yl)piperidine-3,4-diol | ND | ND | 0.791 ± 0.162 | 109.3 ± 3.6 |
| none | IFG-tartrate | 0.271 ± 0.012 | 8.2 ± 0.04 | 0.31 ± 0.11 | 105.5 ± 12.8 |

Notes:
*Stereoisomer A and/or B
Cheng-Prusoff equation: Ki = IC$_{50}$/(1 + [S]/K$_m$) where [S] = substrate concentration; 2.5 mM 4-MU-β-D-Glc was used
K$_m$ = Michaelis constant that defines substrate affinity; 1.8 ± 0.6 mM for 4-MU-β-D-Glc (Liou et al., (2006) J Biol. Chem. 281 (7), 4242-53)

When compared to reference compound IFG-tartrate, the following is notable: (i) test compounds (3R,4R,5S)-5-(difluoromethyl)piperidine-3,4-diol, (3R,4R,5S)-5-(1-fluoroethyl)piperidine-3,4-diol, (3R,4R,5R)-5-(1-hydroxyethyl)-piperidine-3,4-diol, (3R,4R,5S)-5-((R)-1-fluoropropyl)piperidine-3,4-diol hydrochloride, and (3R,4R,5S)-5-benzylpiperidine-3,4-diol, were found to cause a concentration-dependent increase in GCase activity and enhanced enzyme activity to the same maximum level as reference compound IFG-tartrate at much lower concentration; (ii) test compounds (3R,4R,5S)-5-(difluoromethyl)piperidine-3,4-diol, (3R,4R,5S)-5-(1-fluoroethyl)piperidine-3,4-diol, and (3R,4R,5S)-5-benzylpiperidine-3,4-diol, washed out of the lysosomal compartment (in situ washout) considerably faster than reference compound IFG-tartrate; and (iii), test compounds (3R,4R,5S)-5-(difluoromethyl)piperidine-3,4-diol, (3R,4R,5S)-5-(1-fluoroethyl)piperidine-3,4-diol, (3R,4R,5R)-5-(1-hydroxyethyl)-piperidine-3,4-diol, (3R,4R,5R)-5-(1-hydroxyethyl)-piperidine-3,4-diol, (3R,4R,5S)-5-((R)-1-fluoropropyl)piperidine-3,4-diol hydrochloride, and (3R,4R,5S)-5-benzylpiperidine-3,4-diol, inhibited GCase activity.

Example 2

Blood Brain Barrier Penetration

The blood-brain barrier (BBB) penetration of reference compound IFG-tartrate and several compounds of the present invention (i.e., (3R,4R,5S)-5-(difluoromethyl)piperidine-3,4-diol, (3R,4R,5S)-5-(1-fluoroethyl)piperidine-3,4-diol, (3R,4R,5R)-5-(1-hydroxyethyl)-piperidine-3,4-diol, (3R,4R,5S)-5-((R)-1-fluoropropyl)piperidine-3,4-diol hydrochloride, and (3R,4R,5S)-5-benzylpiperidine-3,4-diol) were assayed after oral administration to mice. For this purpose, 8-week old wild-type male mice (C57BL/6) were administered a single 30 mg/kg (free base equivalent) p.o. dose of reference or test compound by gavage (n=3 mice per time point). Dosing solutions were prepared in water. After dosing, mice were euthanized with $CO_2$ at the following time points: 0-, 0.5-, 1-, and 4-hour post-dose. After euthanization, whole blood was collected from the inferior vena cava into lithium heparin tubes. Similarly, brains were collected from each mouse. Plasma was derived by spinning whole blood at 2,700×g for 10 minutes at 4° C. followed by storage on dry ice. Whole brains were washed in cold PBS to remove contaminating blood, blotted dry, flash frozen on dry ice, and ultimately stored at −80° C. until analysis. To prepare brain samples for analysis, 50-100 mg of tissue was homogenized in 400 µl of water/mg tissue. Samples were then clarified by centrifugation. Next, 25 µl of the brain homogenate supernatant or 25 µl of plasma were combined with 25 µl of acetonitrile:water (95/5). This was supplemented with 25 µl of acetonitrile and 50 µl of internal standard (100 ng/mL IFG-tartrate 13C2-15N in 0.5% formic acid in (70:30) acetonitrile:methanol). Samples were again clarified by centrifugation and 75 µl of the supernatant was combined with 75 µl of acetonitrile. Samples were then analyzed for compound levels by LC-MS/MS at PPD Inc. (3230 Deming Way, Middleton, Wis. 53562). In brief, a Thermo Betasil, Silica-100, 50×3 mm, 5µ column equilibrated with a mixture of mobile phase consisting of 5 mM ammonium formate and 0.05% formic acid in (A) 95:5 acetonitrile:water or (B) 70:20:10 methanol:water:acetonitrile was employed. Between 20 and 30 µl sample was injected for analysis. For calculating drug concentrations, raw data for plasma (ng/mL) and brain (ng/g) was converted to nM using the molecular weight of respective compounds and assuming 1 g of tissue is equivalent to 1 mL volume. Concentration as a function of time was plotted in GraphPad Prism version 4.02.

The plasma levels and brain levels detected in mice administered a single 30 mg/kg (free base equivalent) p.o. dose of reference compound (i.e., IFG-tartrate) or test compound (i.e., (3R,4R,5S)-5-(difluoromethyl)piperidine-3,4-diol, (3R,4R,5S)-5-(1-fluoroethyl)piperidine-3,4-diol, (3R,4R,5R)-5-(1-hydroxyethyl)-piperidine-3,4-diol, (3R,4R,5S)-5-((R)-1-fluoropropyl)piperidine-3,4-diol hydrochloride, or (3R,4R,5S)-5-benzylpiperidine-3,4-diol) reflect that (3R,4R,5S)-5-(difluoromethyl)piperidine-3,4-diol, (3R,4R,5S)-5-(1-fluoroethyl)piperidine-3,4-diol, (3R,4R,5S)-5-((R)-1-fluoropropyl)piperidine-3,4-diol hydrochloride, and (3R,4R,5S)-5-benzylpiperidine-3,4-diol crossed the blood brain barrier more readily as compared to IFG-tartrate. Additionally, higher levels of (3R,4R,5S)-5-(difluoromethyl)piperidine-3,4-diol, (3R,4R,5S)-5-(1-fluoroethyl)piperidine-3,4-diol, (3R,4R,5S)-5-((R)-1-fluoropropyl)piperidine-3,4-diol hydrochloride, and (3R,4R,5S)-5-benzylpiperidine-3,4-diol were detected in brain than that observed following administration of IFG-tartrate.

Example 3

GCase Enhancement

The ability of orally administered test compounds ((3R,4R,5S)-5-(difluoromethyl)piperidine-3,4-diol, (3R,4R,5S)-5-(1- fluoroethyl)piperidine-3,4-diol, (3R,4R,5S)-5-((R)-1-fluoropropyl)piperidine-3,4-diol hydrochloride, or (3R,4R,5S)-5-benzylpiperidine-3,4-diol) to elevate GCase levels was assessed in mice. For this purpose, 8-week old wild-type male mice (C57BL/6) were administered a single p.o. (gavage) dose of a compound of the present invention (i.e., (3R,4R,5S)-5-(difluoromethyl)piperidine-3,4-diol, (3R,4R,5S)-5-(1-fluoroethyl)piperidine-3,4-diol, (3R,4R,5S)-5-((R)-1-fluoropropyl)piperidine-3,4-diol hydrochloride, or (3R,4R,5S)-5-benzylpiperidine-3,4-diol). Details of the dose administered for each compound are provided in Tables 3A and 3B. The dosing solutions were prepared in water. Compounds were administered over 2 weeks as follows: week 1, Mon-Fri (On), Sat-Sun (Off); week 2, Mon-Thu (On); necropsy on Friday. Thus, a total of 9 doses (dosing solutions prepared fresh every day) were given to each mouse, with a 24-hour washout between the last dose and necropsy.

After completion of dosing, mice were euthanized with $CO_2$ and whole blood was drawn into lithium heparin tubes from the inferior vena cava. Plasma was collected by spinning blood at 2700 g for 10 minutes at 4° C. Liver, spleen, lung, and brain tissues were removed, washed in cold PBS, blotted dry, flash frozen on dry ice, and stored at −80° C. until analysis. GCase levels were measured by homogenizing approximately 50 mg tissue in 500 μL McIlvane (MI) buffer (100 mM sodium citrate, 200 mM sodium phosphate dibasic, 0.25% sodium taurocholate, and 0.1% Triton X-100, pH 5.2) at pH 5.2 for 3-5 seconds on ice with a micro homogenizer. Homogenates were then incubated at room temperature without and with 2.5 mM conduritol-B-epoxide (CBE) for 30 min. Finally, 3.7 mM 4-methylumbeliferryl-β-glucoside (4-MUG) substrate was added and incubated at 37° C. for 60 min. Reactions were stopped by addition of 0.4 M glycine, pH 10.6. Fluorescence was measured on a plate reader for 1 sec/well using 355 nm excitation and 460 nm emission. Total protein was determined in lysates using the MicroBCA kit according to the manufacturer's instructions. A 4-methylumbelliferone (4-MU) standard curve ranging from 1.0 nM to 50 μM was run in parallel for conversion of raw fluorescence data to absolute GCase activity (in the presence and absence of CBE) and expressed as nanomoles of 4-MU released per milligram of protein per hour (nmol/mg protein/hr). GCase levels and protein levels were calculated using Microsoft Excel (Redmond, Wash.) and GraphPad Prism version 4.02.

Tables 3A and 3B summarize the dose administered for each compound examined in mice as described above as well as the resultant level of GCase enhancement in brain and spleen, respectively, compound concentration in tissue, compound concentration in GCase assay and inhibition constant (Ki).

TABLE 3A

GCase enhancement in Brain

| Compound Name | Dose (mg/kg) FBE | GCase increase (fold) | Compound concentration in tissue2.2 nmol/kg | Compound concentration in GCase assay (μM) | Ki pH 5.2 (uM) |
|---|---|---|---|---|---|
| (3R,4R,5S)-5-(difluoromethyl)-piperidine-3,4-diol | 10 | 2.1 | 55 | 0.0002 | 0.0136 ± 0.0008 |
| (3R,4R,5S)-5-(difluoromethyl)-piperidine-3,4-diol | 100 | 2.6 | 301 | 0.0010 | |
| (3R,4R,5S)-5-(1-fluoroethyl)-piperidine-3,4-diol* | 10 | 1.5 | 50 | 0.0002 | 0.0498 ± 0.0015 |
| (3R,4R,5S)-5-(1-fluoroethyl)-piperidine-3,4-diol* | 100 | 2.4 | 415 | 0.0014 | |
| (3R,4R,5R)-5-(1-hydroxyethyl)-piperidine-3,4-diol* | ND | ND | ND | ND | 0.044 ± 0.0017 |
| (3R,4R,5R)-5-(1-hydroxyethyl)-piperidine-3,4-diol* | ND | ND | ND | ND | 0.142 ± 0.0088 |
| (3R,4R,5S)-5-(1-fluoroethyl)-piperidine-3,4-diol* | 10 | 1.5 | BLQ(1) | BLQ | 0.016 ± 0.0007 |
| (3R,4R,5S)-5-(1-fluoroethyl)-piperidine-3,4-diol* | 100 | 2.2 | 41 | 0.0001 | |
| (3R,4R,5S)-5-((R)-1-fluoropropyl)-piperidine-3,4-diol hydrochloride | 10 | 0.9 | BLQ(2) | BLQ | 0.121 ± 0.0026 |
| (3R,4R,5S)-5-((R)-1-fluoropropyl)-piperidine-3,4-diol hydrochloride | 100 | 1.1 | 38 | 0.0001 | |
| (3R,4R,5S)-5-benzyl-piperidine-3,4-diol | 10 | 1.2 | ND | ND | 0.273 ± 0.012 |
| (3R,4R,5S)-5-benzyl-piperidine-3,4-diol | 100 | 1.4 | ND | ND | |

TABLE 3A-continued

GCase enhancement in Brain

| Compound Name | Dose (mg/kg) FBE | GCase increase (fold) | Compound concentration in tissue 2.2 nmol/kg | Compound concentration in GCase assay (μM) | Ki pH 5.2 (uM) |
|---|---|---|---|---|---|
| (3R,4R,5R)-5-((S)-hydroxy(phenyl)methyl)-piperidine-3,4-diol | ND | ND | ND | ND | 1.36 ± 0.10 |
| (3R,4R,5S)-5-(2-hydroxypropan-2-yl)piperidine-3,4-diol | ND | ND | ND | ND | 0.097 ± 0.0015 |

Notes:
*Stereoisomer A and/or B
(1) BLQ < 7.4 nmol/kg;
(2) BLQ < 2.2 nmol/kg
ND: Not determined

TABLE 3B

GCase enhancement in Spleen

| Compound Name | Dose (mg/kg) FBE | GCase increase (fold) | Compound concentration in tissue | Compound concentration in GCase assay | Ki pH 5.2 (uM) |
|---|---|---|---|---|---|
| (3R,4R,5S)-5-(difluoromethyl)-piperidine-3,4-diol | 10 | 1.9 | 100 | 0.0003 | 0.0136 ± 0.0008 |
| (3R,4R,5S)-5-(difluoromethyl)-piperidine-3,4-diol | 100 | 2.4 | 435 | 0.0015 | |
| (3R,4R,5S)-5-(1-fluoroethyl)-piperidine-3,4-diol* | 10 | 1.0 | BLQ(1) | BLQ | 0.0498 ± 0.0015 |
| (3R,4R,5S)-5-(1-fluoroethyl)-piperidine-3,4-diol* | 100 | 1.5 | 948 | 0.0032 | |
| (3R,4R,5R)-5-(1-hydroxyethyl)-piperidine-3,4-diol* | ND | ND | ND | ND | 0.044 ± 0.0017 |
| (3R,4R,5R)-5-(1-hydroxyethyl)-piperidine-3,4-diol* | ND | ND | ND | ND | 0.142 ± 0.0088 |
| (3R,4R,5S)-5-(1-fluoroethyl)-piperidine-3,4-diol* | 10 | 1.6 | BLQ(2) | BLQ | 0.016 ± 0.0007 |
| (3R,4R,5S)-5-(1-fluoroethyl)-piperidine-3,4-diol* | 100 | 2.3 | 99 | 0.0003 | |
| (3R,4R,5S)-5-((R)-1-fluoropropyl)-piperidine-3,4-diol hydrochloride | 10 | 0.7 | 21 | 0.0001 | 0.121 ± 0.0026 |
| (3R,4R,5S)-5-((R)-1-fluoropropyl)-piperidine-3,4-diol hydrochloride | 100 | 0.7 | 60 | 0.0002 | |
| (3R,4R,5S)-5-benzyl-piperidine-3,4-diol | 10 | 1.0 | ND | ND | 0.273 ± 0.012 |
| (3R,4R,5S)-5-benzyl-piperidine-3,4-diol | 100 | 1.2 | ND | ND | |
| (3R,4R,5R)-5-((S)-hydroxy(phenyl)methyl)-piperidine-3,4-diol | ND | ND | ND | ND | 1.36 ± 0.10 |
| (3R,4R,5S)-5-(2-hydroxypropan-2-yl)piperidine-3,4-diol | ND | ND | ND | ND | 0.097 ± 0.0015 |

Notes:
*Stereoisomer A and/or B
(1) BLQ < 6.8 nmol/kg;
(2) BLQ < 7.9 nmol/kg
ND: Not determined As reflected in Tables 3A and 3B, mice administered (3R,4R,5S)-5-(difluoromethyl)piperidine-3,4-diol, (3R,4R,5S)-5-(1-fluoroethyl)piperidine-3,4-diol, or (3R,4R,5S)-5-benzylpiperidine-3,4-diol demonstrated significant GCase enhancement in brain and spleen.

Example 4

Rat Pharmacokinetics

Pharmacokinetic (PK) data was obtained in rats to assess the bioavailability of test compound. In particular, the following PK parameters were calculated: bioavailability as measured by area under the Concentration/Time curve (AUC), fraction of dose available (% F; further defined below), clearance (CL), volume of distribution (Vd), and half-life (t½). For this purpose, 8-week old Sprague-Dawley male rats were given either a single intravenous (IV) dose equivalent to 3 mg/kg of free base or single escalating p.o. (gavage) doses of test compound equivalent to 10, 30, and 100 mg/kg of free base. Three rats were used per dosing group. Blood was collected over a 24-hr period. The time points for blood collection after intravenous administration were: 0, 2.5, 5, 10, 15, 30, 45 min, 1, 2, 4, 8, 12, and 24 hrs; time points for blood collection after p.o. administrations were: 0, 5, 15, 30, 45 min, 1, 2, 3, 4, 8, 12, and 24 hrs. Plasma samples were analyzed for compound levels by LC-MS/MS at PPD. Raw data was analyzed by non-compartmental analysis in Win-nonLin to calculate $V_D$, % F, CL, and $t_{1/2}$.

Various pharmacokinetic parameters for (3R,4R,5S)-5-(difluoromethyl)piperidine-3,4-diol, (3R,4R,5S)-5-(1-fluoroethyl)piperidine-3,4-diol, and (3R,4R,5S)-5-benzylpiperidine-3,4-diol based on the aforementioned study are detailed below in Tables 4A-D.

TABLE 4A

Rat PK for (3R,4R,5S)-5-(difluoromethyl)piperidine-3,4-diol-HCl

| Dose (mg/kg) | | | | | | | | |
|---|---|---|---|---|---|---|---|---|
| Salt | Free Base | Route | $AUC_{last}$ (hr*ng/ml) | % F | $t_{1/2}$(h) | $C_{max}$ (ng/mL) | CL (mL/hr/kg) | $V_D$ (mL/kg) |
| 3.65 | 3 | IV | $AUC_{0-12\,hr}$ 2044 ± 294 | N/A | 1.1 ± 0.05 | 2323 ± 348 | 1555 ± 218 | 2612 ± 269 |
| 12.18 | 10 | PO | $AUC_{0-12\,hr}$ 6714 ± 524 | 106 ± 8.6 | 2.58 ± 0.78 | 3363 ± 219 | N/A | N/A |
| 36.54 | 30 | PO | $AUC_{0-24\,hr}$ 21685 ± 1515 | 101 ± 6.9 | 2.75 ± 0.36 | 10037 ± 865 | N/A | N/A |
| 121.81 | 100 | PO | $AUC_{0-24\,hr}$ 79389 ± 8570 | 121 ± 12.9 | 2.41 ± 0.16 | 33200 ± 4990 | N/A | N/A |

Notes:

Non compartmental analysis mean values (N = 3 rats)

BLD Below Limit of Detection (<0.5 ng/mL)

BLQ Below Limit of Quantitation $$\% F = \frac{AUC\ PO \times 100\ dose\ normalized}{AUC\ IV}$$

$AUC_{last}$ = Area under the Concentration/Time curve to the last data point

TABLE 4B

Rat PK for (3R,4R,5S)-5-(1-fluoroethyl)piperidine-3,4-diol-HCl*

| Dose (mg/kg) | | | | | | | | |
|---|---|---|---|---|---|---|---|---|
| Salt | Free Base | Route | $AUC_{last}$ (hr * ng/ml) | % F | $t_{1/2}$ (h) | $C_{max}$ (ng/mL) | CL (mL/hr/kg) | $V_D$ (mL/kg) |
| 3.67 | 3 | IV | $AUC_{0-24\,hr}$ 1421 ± 188.1 | N/A | 2.6 ± 0.64 | 2328 ± 373 | 2708 ± 410 | 9774 ± 1551 |
| 12.23 | 10 | PO | $AUC_{0-24\,hr}$ 7097 ± 606 | 148 ± 12.5 | 2.8 ± 0.50 | 2680 ± 167 | N/A | N/A |
| 36.70 | 30 | PO | $AUC_{0-24\,hr}$ 21664 ± 1708 | 155 ± 12.2 | 2.7 ± 0.12 | 6917 ± 451 | N/A | N/A |
| 122.34 | 100 | PO | $AUC_{0-24\,hr}$ 59481 ± 1005 | 142 ± 2.5 | 2.5 ± 0.19 | 19433 ± 3031 | N/A | N/A |

Note:

*Stereoisomer A and/or B

TABLE 4C

Rat PK for (3R,4R,5S)-5-(1-fluoroethyl)piperidine-3,4-diol-HCl*

Dose (mg/kg)

| Salt | Free Base | Route | AUC$_{last}$ (hr * ng/ml) | % F | t$_{1/2}$ (h) | C$_{max}$ (ng/mL) | CL (mL/hr/kg) | V$_D$ (mL/kg) |
|---|---|---|---|---|---|---|---|---|
| 3.67 | 3 | IV | AUC$_{0-24\ hr}$ 1370 ± 109 | N/A | 2.06 ± 0.47 | 2427 ± 192 | 2188 ± 173 | 6304 ± 927 |
| 12.23 | 10 | PO | AUC$_{0-24\ hr}$ 4251 ± 88 | 98 ± 1.85 | 3.0 ± 0.22 | 1127 ± 60 | N/A | N/A |
| 36.70 | 30 | PO | AUC$_{0-24\ hr}$ 14229 ± 127 | 104 ± 0.88 | 2.6 ± 0.16 | 4680 ± 369 | N/A | N/A |
| 122.34 | 100 | PO | AUC$_{0-24\ hr}$ 50946 ± 713 | 104 ± 1.5 | 2.4 ± 0.16 | 15733 ± 622 | N/A | N/A |

Note:
*Stereoisomer A and/or B

TABLE 4D

Rat PK for (3R,4R,5S)-5-benzylpiperidine-3,4-diol-HCl

Dose (mg/kg)

| Salt | Free Base | Route | AUC$_{last}$ (hr * ng/ml) | % F | t$_{1/2}$ (h) | C$_{max}$ (ng/mL) | CL (mL/hr/kg) | V$_D$ (mL/kg) |
|---|---|---|---|---|---|---|---|---|
| 3.53 | 3 | IV | AUC$_{0-12\ hr}$ 592 ± 60.9 | N/A | 1.7 ± 1.5 | 969 ± 104 | 5145 ± 532 | 12570 ± 1792 |
| 11.76 | 10 | PO | AUC$_{0-24\ hr}$ 1200 ± 46.4 | 61.7 ± 2.4 | 3.86 ± 0.6 | 641 ± 48.7 | N/A | N/A |
| 35.28 | 30 | PO | AUC$_{0-24\ hr}$ 3690 ± 71.5 | 62.3 ± 1.2 | 3.8 ± 0.19 | 1703 ± 133 | N/A | N/A |
| 117.59 | 100 | PO | AUC$_{0-24\ hr}$ 13519 ± 2177 | 68.3 ± 10.8 | 2.9 ± 0.11 | 7140 ± 1357 | N/A | N/A |

As reflected in Tables 4A-D, (3R,4R,5S)-5-(difluoromethyl)piperidine-3,4-diol, (3R,4R,5S)-5-(1-fluoroethyl)piperidine-3,4-diol, and (3R,4R,5S)-5-benzylpiperidine-3,4-diol have favorable pharmacokinetic profiles for drug development. In particular, (3R,4R,5S)-5-(difluoromethyl)piperidine-3,4-diol, (3R,4R,5S)-5-(1-fluoroethyl)piperidine-3,4-diol, and (3R,4R,5S)-5-benzylpiperidine-3,4-diol show excellent oral bioavailability (approximately 50-100%) and dose proportionality, a half-life of 1.0 to 4.0 hours, and a volume of distribution suggesting adequate penetration into peripheral tissues.

What is claimed:
1. A compound selected from the following:

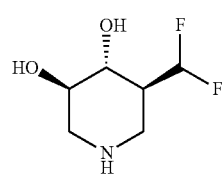

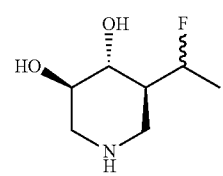

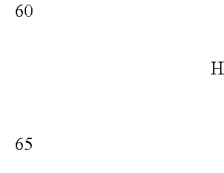

-continued

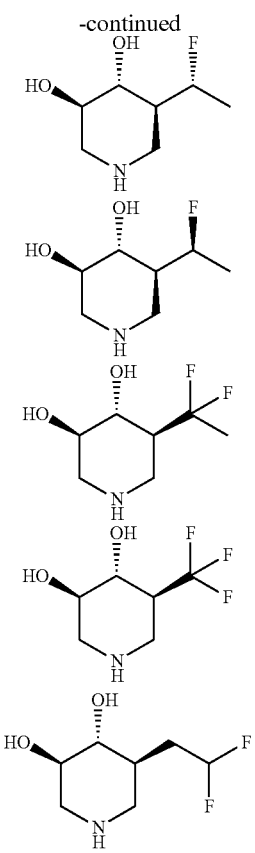

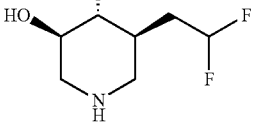

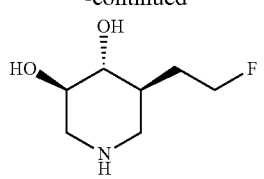
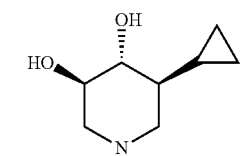
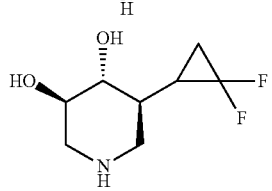
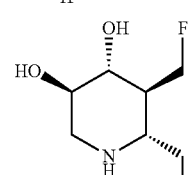
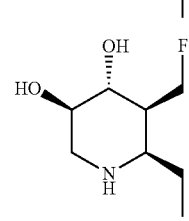
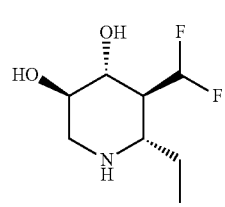
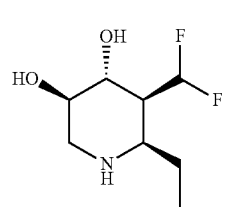
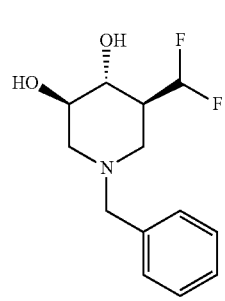
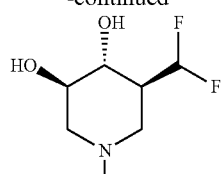
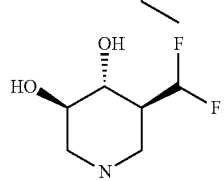
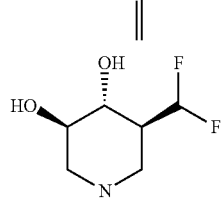
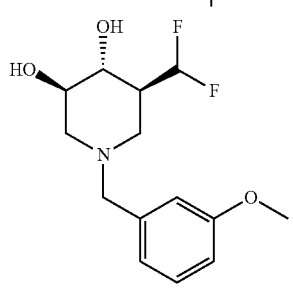
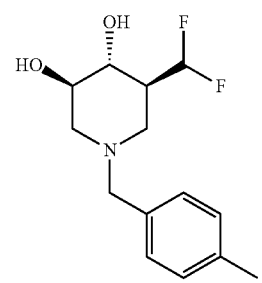
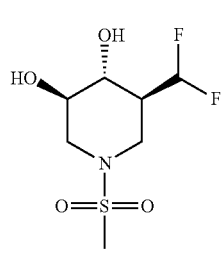

-continued
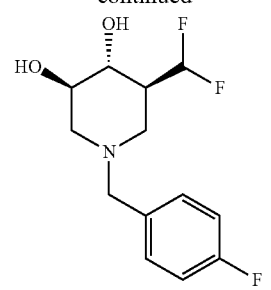
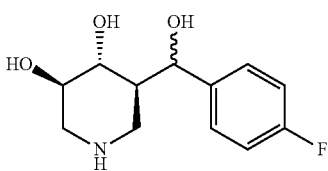
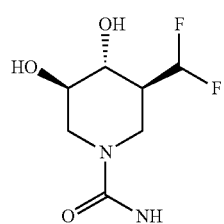
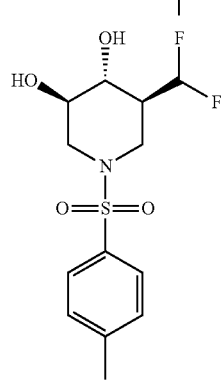
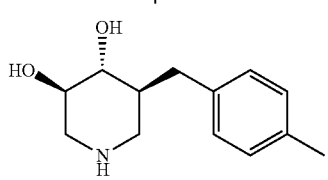
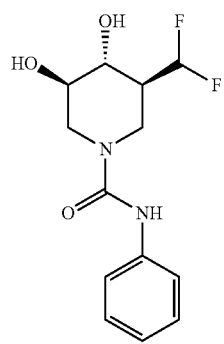
-continued
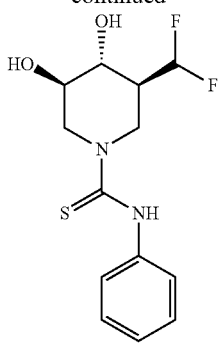
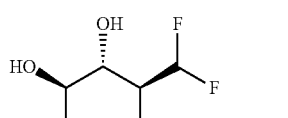
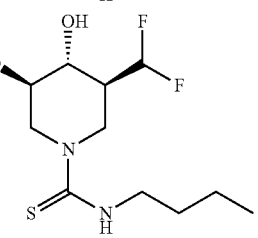
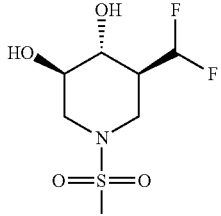
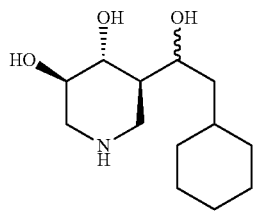
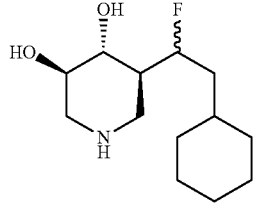
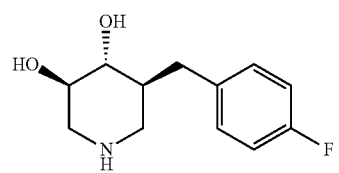

-continued

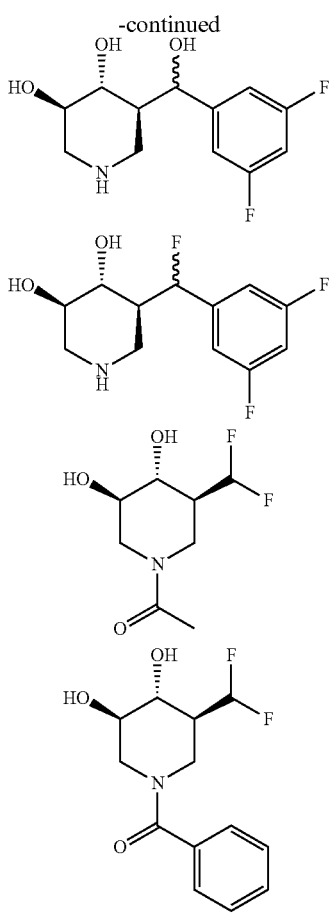

or a pharmaceutically acceptable salt, or solvate thereof.
2. The compound of claim 1 which is:

3. The compound of claim 1 which is:

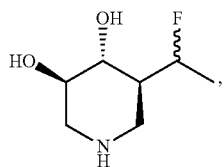

or a pharmaceutically acceptable salt, or solvate thereof.
4. The compound of claim 1 which is:

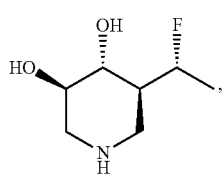

or a pharmaceutically acceptable salt, or solvate thereof.
5. The compound of claim 1 which is:

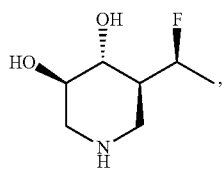

or a pharmaceutically acceptable salt, or solvate thereof.
6. A pharmaceutical composition comprising at least one pharmaceutically acceptable carrier and a compound selected from:

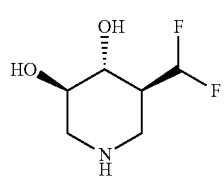 [SMILES: O[C@H]1[C@H](O)CNC[C@@H]1C(F)F]

or a pharmaceutically acceptable salt, or solvate thereof.
7. A pharmaceutical composition comprising at least one pharmaceutically acceptable carrier and a compound selected from:

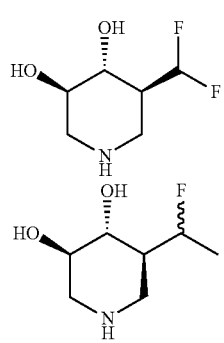

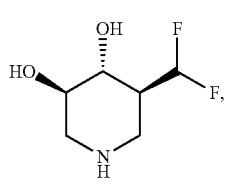

or a pharmaceutically acceptable salt, or solvate thereof.

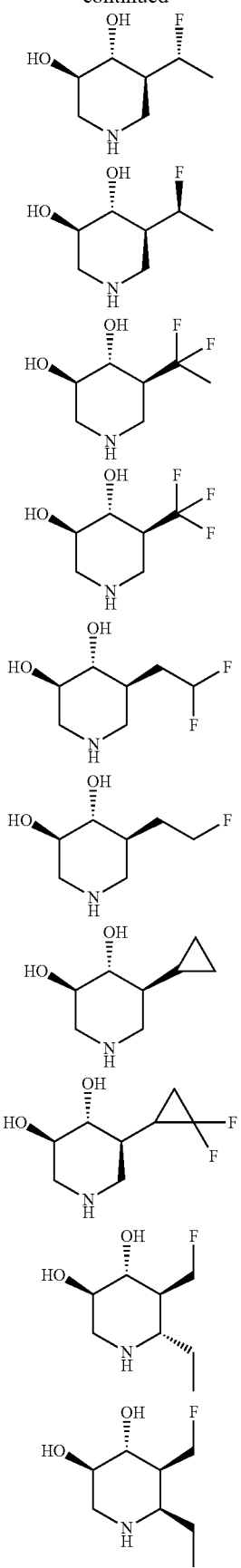
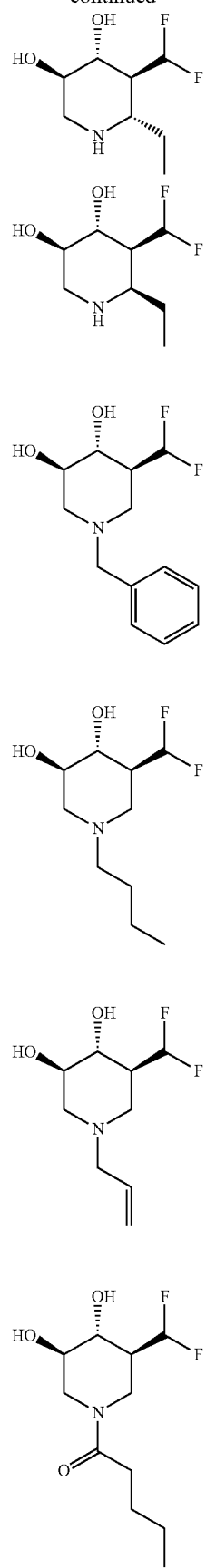

-continued
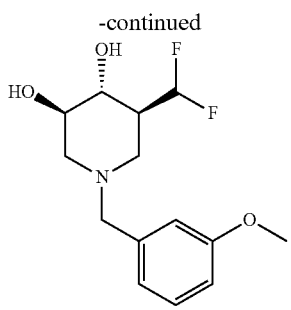
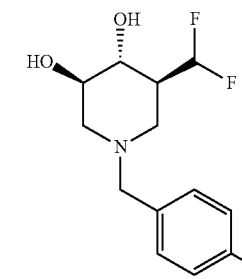
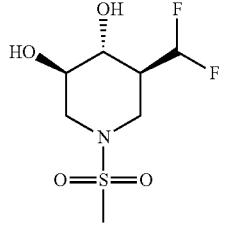
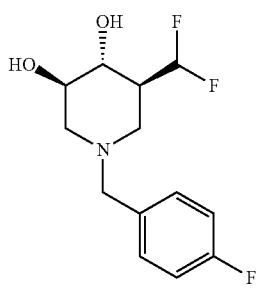
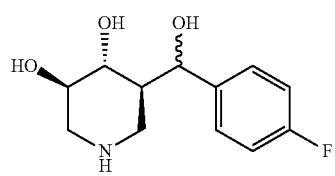
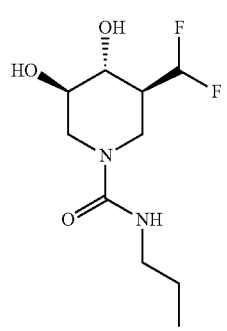
-continued
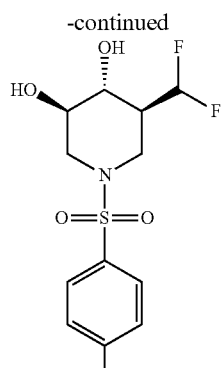
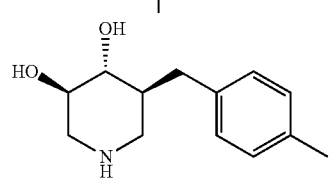
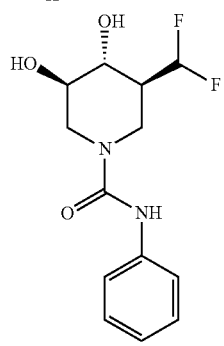
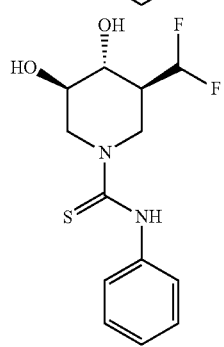
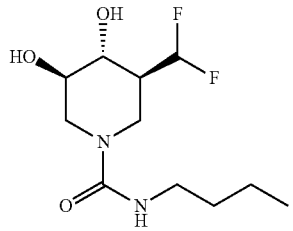
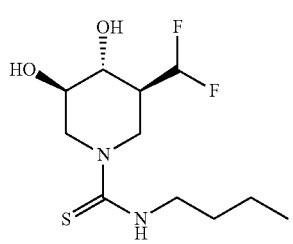

-continued

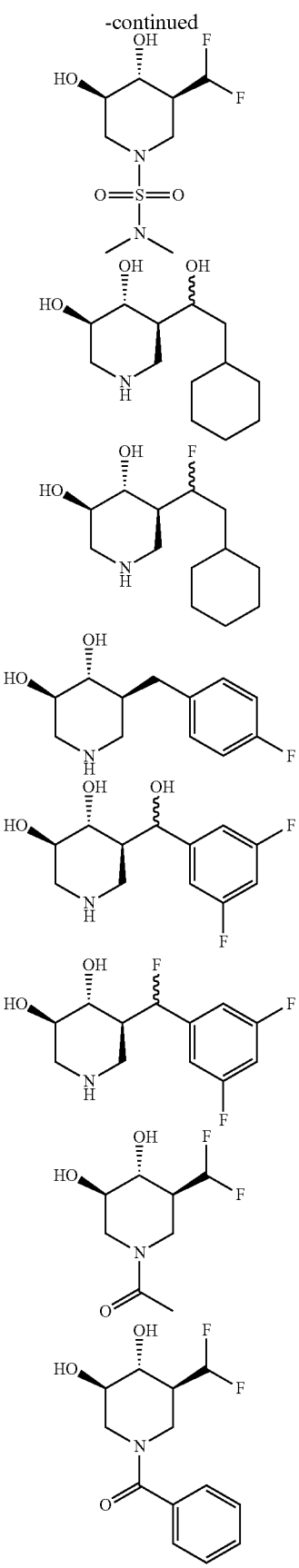

-continued

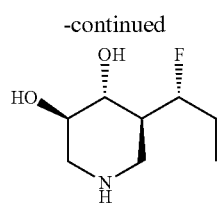

or a pharmaceutically acceptable salt, or solvate thereof.

8. The pharmaceutical composition of claim 7, wherein the compound is:

[structure]

or a pharmaceutically acceptable salt, or solvate thereof.

9. The pharmaceutical composition of claim 7, wherein the compound is:

[structure]

or a pharmaceutically acceptable salt, or solvate thereof.

10. The pharmaceutical composition of claim 7, wherein the compound is:

[structure]

or a pharmaceutically acceptable salt, or solvate thereof.

* * * * *